(12) United States Patent
Wilson et al.

(10) Patent No.: US 8,986,942 B2
(45) Date of Patent: Mar. 24, 2015

(54) CARBON NANOTUBE BASED IMAGING AGENTS

(75) Inventors: Lon J. Wilson, Houston, TX (US); Kyle Ryan Kissell, Manvel, TX (US); Keith Bennett Hartman, McLean, VA (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 13/473,120

(22) Filed: May 16, 2012

(65) Prior Publication Data

US 2013/0130295 A1     May 23, 2013

Related U.S. Application Data

(60) Division of application No. 12/274,174, filed on Nov. 19, 2008, now abandoned, which is a continuation of application No. PCT/US2007/069459, filed on May 22, 2007.

(60) Provisional application No. 60/747,874, filed on May 22, 2006.

(51) Int. Cl.
*A61K 49/04* (2006.01)
*B82Y 5/00* (2011.01)
*C01B 31/22* (2006.01)
*A61K 49/06* (2006.01)
*A61K 51/00* (2006.01)

(52) U.S. Cl.
CPC .............. *A61K 51/00* (2013.01); *A61K 49/0409* (2013.01); *A61K 49/0447* (2013.01); *B82Y 5/00* (2013.01)
USPC ........................................ 435/29; 423/447.1

(58) Field of Classification Search
None
See application file for complete search history.

(56) References Cited

U.S. PATENT DOCUMENTS

| | | | | |
|---|---|---|---|---|
| 5,688,486 | A * | 11/1997 | Watson et al. | 424/1.65 |
| 6,660,248 | B2 * | 12/2003 | Wilson et al. | 424/9.4 |
| 2003/0157016 | A1 * | 8/2003 | Bolskar et al. | 423/461 |
| 2006/0051290 | A1 * | 3/2006 | Wilson et al. | 424/1.11 |

OTHER PUBLICATIONS

Bianco et al., Current Opinion in Chemical Biology, vol. 9, pp. 674-679 (electronically available Oct. 17, 2005).*
Kam et al., Journal of American Chemical Society, vol. 127, pp. 6021-6026 (electronically available Mar. 31, 2005).*
Bianco et al., Current Opinion in Chemical Biology, vol. 9, pp. 674-679 (electronically available Oct. 17, 2005; of record).*
Kam et al., Journal of American Chemical Society, vol. 127, pp. 6021-6026 (electronically available Mar. 31, 2005; of record).*
Popov et al., Chemical Reviews, vol. 113, pp. 5989-6113; 2013.*
Alper, J. ("Nanotubes Poised to Help Cancer Patients," National Cancer Institute-NCI Alliance for Nanotechnology in Cancer, pp. 1-4 Jan./Feb. 2006: Accessed: http://nano.cancer.gov/action/news/featurestories/monthly_feature_2006_jan.pdf).*

* cited by examiner

*Primary Examiner* — Cherie M Stanfield
*Assistant Examiner* — Paul D. Pyla
(74) *Attorney, Agent, or Firm* — Robert R. Riddle; Reed Smith LLP

(57) ABSTRACT

Compositions and methods related to carbon nanotubes are provided. More particularly, imaging agents comprising carbon nanotubes internally loaded with a contrast agent and associated methods are provided. One example of a method may involve a method for imaging comprising: providing an imaging agent comprising a carbon nanotube loaded with contrast agent; introducing the imaging agent into a cell; and imaging the cell to detect the presence of the imaging agent.

5 Claims, 18 Drawing Sheets

| Red | Surface Distance | 2.261 µm |
|---|---|---|
| | Horiz distance(L) | 2.220 µm |
| | Vert distance | 81.165 nm |
| | Angle | 2.094° |
| Green | Surface distance | 2.164 µm |
| | Horiz distance | 2.146 µm |
| | Vert distance | 38.412 nm |
| | Angle | 1.025° |
| White | Surface distance | 3.144 µm |
| | Horizon distance | 3.117 µm |
| | Vert distance | 45.361 nm |
| | Angle | 0.834° |

| Red | Surface Distance | 422.67 nm |
| --- | --- | --- |
| | Horiz distance(L) | 422.65 nm |
| | Vert distance | 0.768 nm |
| | Angle | 0.104° |
| Green | Surface distance | 370.82 nm |
| | Horiz distance | 370.37 nm |
| | Vert distance | 1.110 nm |
| | Angle | 0.172° |
| White | Surface distance | 798.39 nm |
| | Horizon distance | 795.97 nm |
| | Vert distance | 1.657 nm |
| | Angle | 0.119° | a　　　　　　　　　b　　　　　　　　　c

| Red | Surface Distance | 29.919 nm |
|---|---|---|
|  | Horiz distance(L) | 27.344 nm |
|  | Vert distance | 7.7655 nm |
|  | Angle | 15.854° |
| Green | Surface distance | 37.077 nm |
|  | Horiz distance | 31.250 nm |
|  | Vert distance | 3.815 nm |
|  | Angle | 6.961° |
| White | Surface distance | 22.462 nm |
|  | Horizon distance | 19.531 nm |
|  | Vert distance | 7.914 nm |
|  | Angle | 22.058° |

| Red | Surface Distance | 31.287 nm |
|---|---|---|
| | Horiz distance(L) | 31.250 nm |
| | Vert distance | 0.750 nm |
| | Angle | 1.374° |
| Green | Surface distance | 19.643 nm |
| | Horiz distance | 19.531 nm |
| | Vert distance | 1.248 nm |
| | Angle | 3.656° |
| White | Surface distance | 27.354 nm |
| | Horizon distance | 27.344 nm |
| | Vert distance | 0.514 nm |
| | Angle | 1.076° | a  b  c

CARBON NANOTUBE BASED IMAGING AGENTS

CROSS-REFERENCE TO RELATED APPLICATIONS

This application is a divisional of U.S. patent application Ser. No. 12/274,174, filed Nov. 19, 2008 now abandoned, which is a continuation of International Application No. PCT/US2007/069459, filed May 22, 2007, which claims the benefit of U.S. Provisional Application Ser. No. 60/747,874, filed May 22, 2006, all of which are incorporated in this application by reference.

BACKGROUND

The discovery of the "buckyball" by Smalley et al. at Rice in 1985 and its cousin the single-walled carbon nanotube (SWNT) by Sumio Iijima in 1991 has sparked two decades of intense research on possible applications of these novel nanostructures. SWNTs have useful properties, such as high tensile strength, low density, high electrical conductivity, and high thermal conductivity. SWNTs have demonstrated the ability to translocate into cells opening the possibility of intracellular diagnostic and therapeutic applications.

One such application, computed tomography (CT), sometimes known as computed axial tomography (CAT), is a powerful diagnostic imaging tool utilized in thousands of diagnoses annually. In CT, imaging is achieved by measuring the attenuation of an X-ray, defined as the loss of energy of the radiant beam due to absorption, scattering, and beam divergence as it propagates through a medium. X-ray slice data is generated by rotating an X-ray source around an object. Detectors opposite the source measure the intensity of the exiting X-ray, which is directly proportional to the radiodensity of the scanned object. The X-ray slices can then be reconstructed into a three-dimensional image for interpretation. Naturally radiodense objects, such as bone, can be easily distinguished from fatty tissue using unenhanced CT. However, for objects with similar radiodensities, such as cancerous tissue compared to healthy tissue, a contrast agent usually needs to be employed to achieve the correct diagnosis.

The majority of existing commercial CT contrast agents are iodine-based because of two factor: iodine is an effective X-ray scatterer due to its large number of electrons (atomic number 53) and current clinical CT X-ray sources operate at 33 keV, an energy which is also absorbed by the iodine atoms; thereby improving the overall performance of the contrast agent. The increase in attenuation at 33 keV for iodine is due to the photoelectric absorption of X-rays at that specific energy by iodine inner-shell electrons.

Many existing CT contrast agents consist of a 1,3,5 tri-iodo benzene backbone with the other three positions on the benzene ring consisting of water-solubilizing groups containing alcohol, amine, amide, and carbonyl functional groups. The major difference between the various contrast agents on the market is the structure of the water-solubilizing groups, but the tri-iodo benzene backbone is nearly universal. These CT agents contain between 25 and 50 percent by mass iodine, have high water solubility, on the order of 150 mg/mL, and are known as blood pool agents. This means the agent circulates in the blood pool, but does not translocate into the interior of cells. Sufficient contrast is achieved solely because abnormal tissues, such as cancerous tumors, require increased blood flow to sustain their growth, resulting in higher local concentrations of contrast agent. Current CT contrast agents are generally not targeted to specific cell types which lead to limitations in the detection of diseases such as vulnerable plaque in the coronary artery.

SUMMARY

The present disclosure relates to compositions and methods related to carbon nanotubes. More particularly, the present disclosure relates to an imaging agent comprising carbon nanotubes internally loaded with a contrast agent and associated methods of preparation and use.

The hollow structure of SWNTs may be used as a capsule to deliver diagnostic and/or therapeutic agents to specific cell-types of interest, such as cancers.

Existing CT technology lacks the ability to non-invasively diagnose critical diseases, such as coronary artery disease vulnerable plaque. The imaging agents of the present disclosure may be used as blood pool CT contrast agents, with long circulation times, avoiding the use of a catheter during x-ray angiography.

By using a carbon nanotube as the base structure of the imaging agent, toxic contrast agents, such as $I_2$ may be sequestered within the interior of the nanotube. This may be advantageous for in vivo applications, to ensure the iodine toxicity is completely sequestered within the interior of the carbon nanotube. The exterior of the nanotube may be substituted with peptides, water-solubilizing groups, and the like, to enhance the ability of the nanotube to be internalized by cells.

The features and advantages of the present disclosure will be readily apparent to those skilled in the art upon a reading of the description of the embodiments that follows.

DRAWINGS

Some specific example embodiments of the disclosure may be understood by referring, in part, to the following description and the accompanying drawings.

Figure 12:
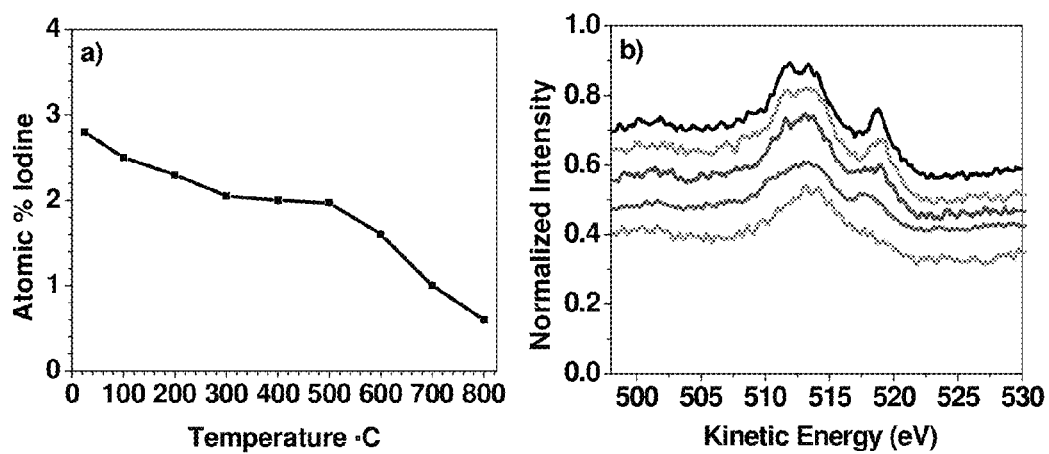

FIG. 12 shows a) Variable-temperature XPS study of $I_2$-SWNTs under high vacuum and b) X-ray induced Auger emission spectrum of $I_2$-SWNTs at room temperature (black), at 100° C. (green), at 200° C. (blue), at 300° C. (red), and reduced by the Na°/THF reduction reaction (yellow). All spectra were acquired under high vacuum. Possible instrument error is ±10° C. and ±0.1% Iodine.

Figure 13:
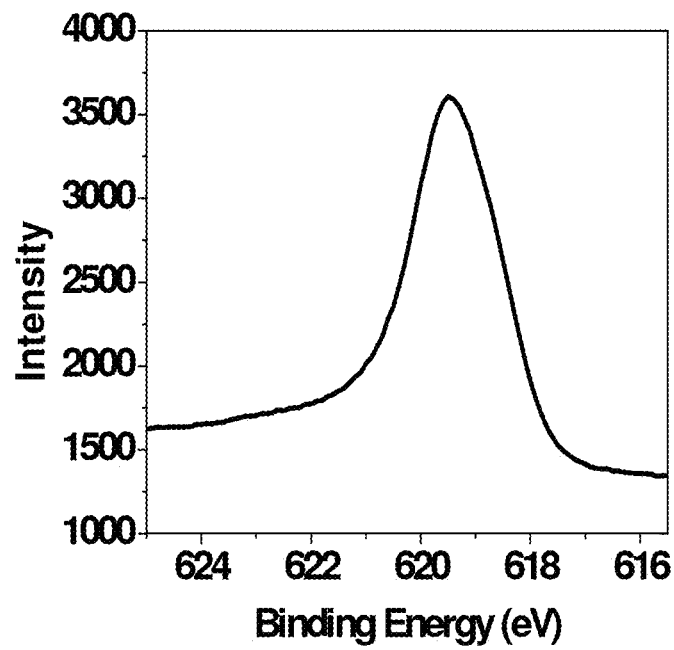

FIG. 13 shows an I $3d_{5/2}$ XPS spectrum for twice-Na°/THF-reduced $I_2$-SWNTs.

Figure 14:
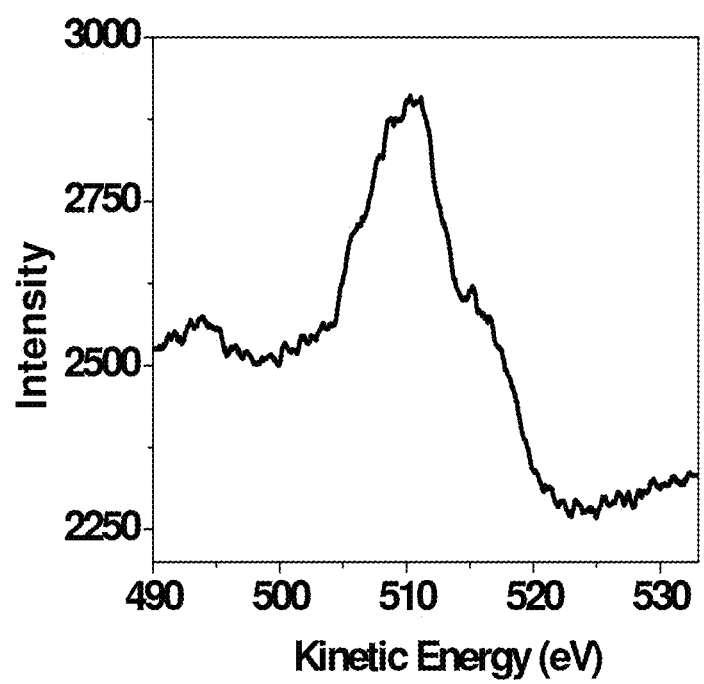
Figure 15:
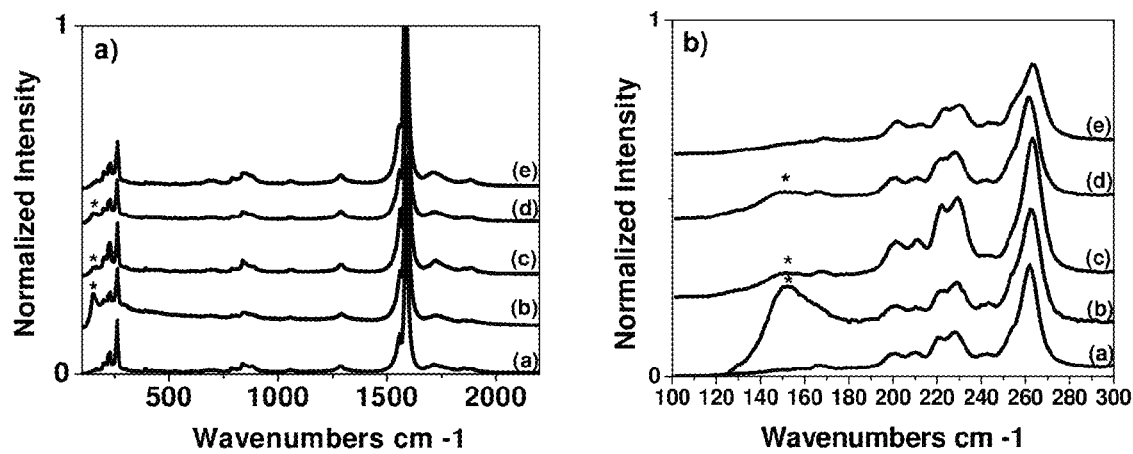

FIG. 14 shows an x-ray induced Auger emission spectrum over the I MNN region for twice-Na°/THF-reduced $I_2$-SWNTs FIG. 15 shows a) Raman spectrum of raw (a) raw SWNTs, (b) $I_2$-SWNTs, (c) Na°/THF reduced $I_2$-SWNTs, (d) $I_2$-SWNTs heated to 400° C., and (e) $I_2$-SWNTs heated to 1000° C. b) The low energy region of a) magnified. The ν (I-I) stretching mode peak is denoted by an asterisk.

Figure 16:
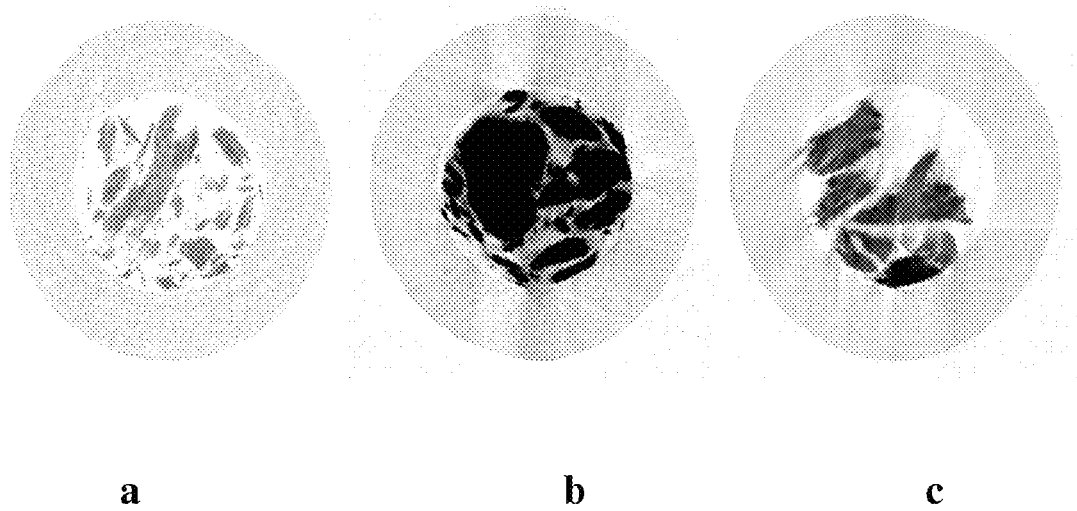

FIG. 16 shows micro CT images of (a) raw SWNTs, (b) $I_2$-SWNTs, and (c) Na°/THF reduced $I_2$@SWNTs.

Figure 17:
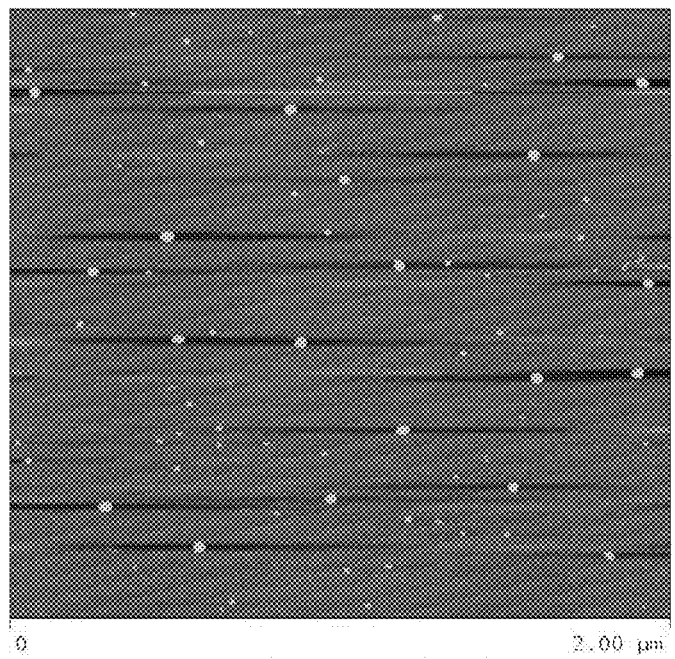

FIG. 17 shows AFM image of US-tubes. Only 20-40 nm in length, the US-tubes are seen as bright dots in a 2 μm² image.

Figure 18:
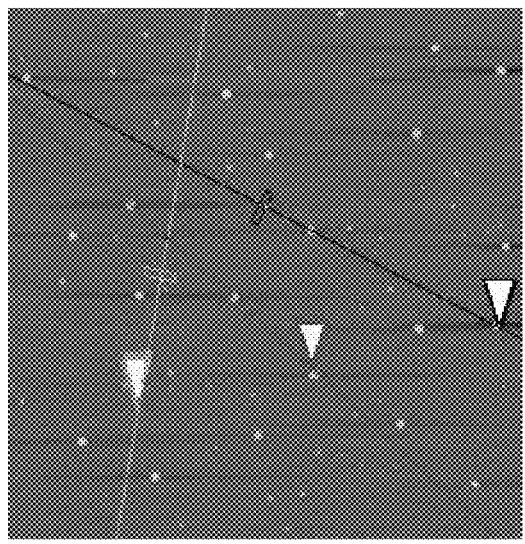

FIG. 18 shows AFM height measurements for US-tubes.

Figure 19:
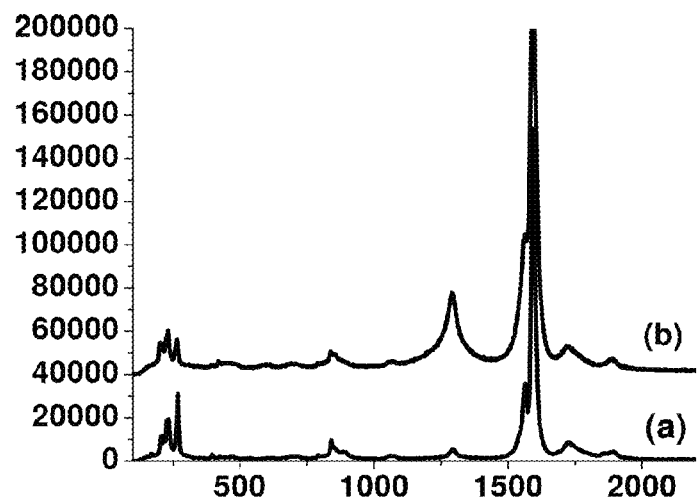

FIG. 19 shows a Raman spectrum of (a) raw SWNTs and (b) US-tubes.

Figure 20:
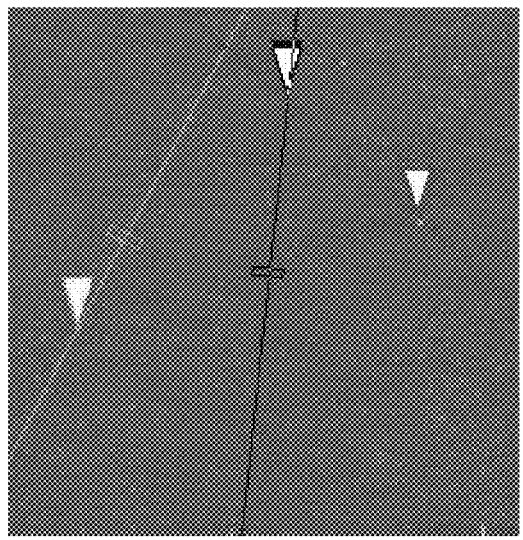

FIG. 20 shows AFM height measurements for Na°/THF reduced US-tubes

Figure 21:
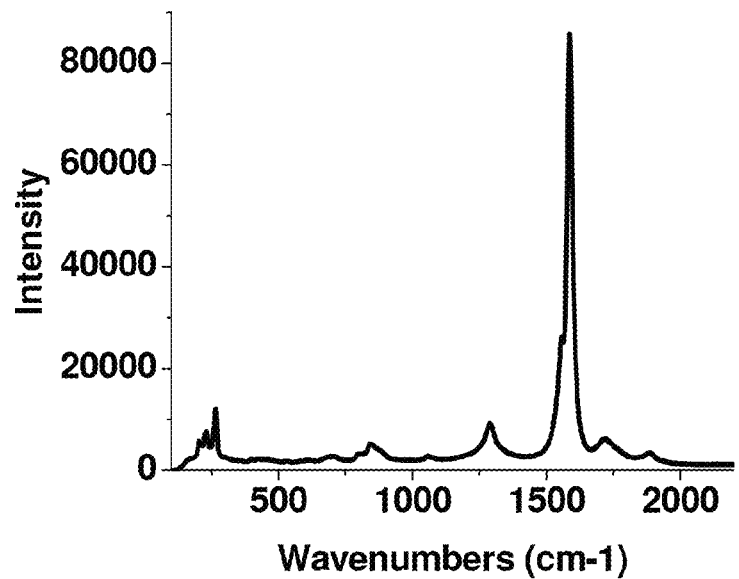

FIG. 21 shows Raman spectrum of $I_2$-US-tubes.

Figure 22:
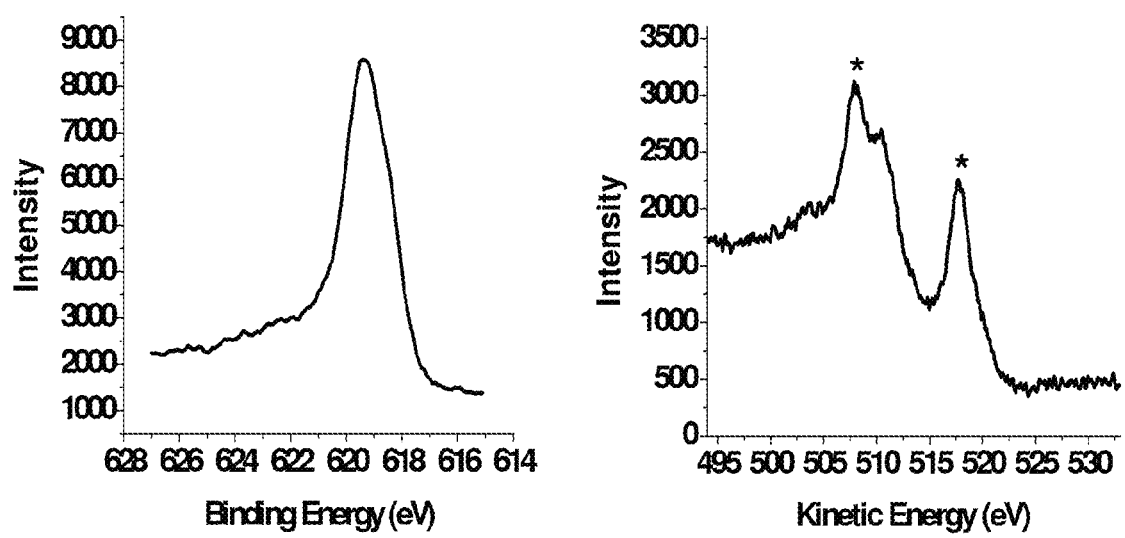

FIG. 22 shows an XPS spectrum (left) and X-ray induced Auger emission spectrum (right) of $I_2$-US-tubes. In the Auger emission spectrum, the peaks assigned previously to external $I_2$ for full-length $I_2$-SWNTs are denoted by asterisks.

Figure 23:
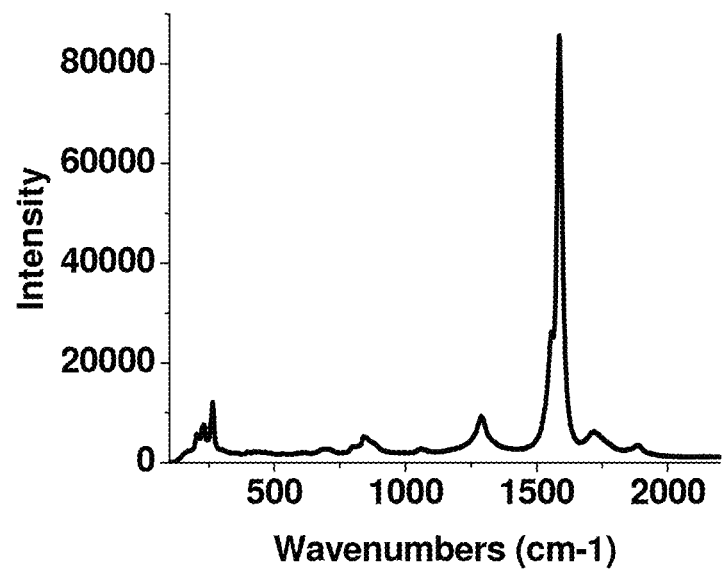

FIG. 23 shows a Raman spectrum of Na°/THF reduced $I_2$-US-tubes.

Figure 24:
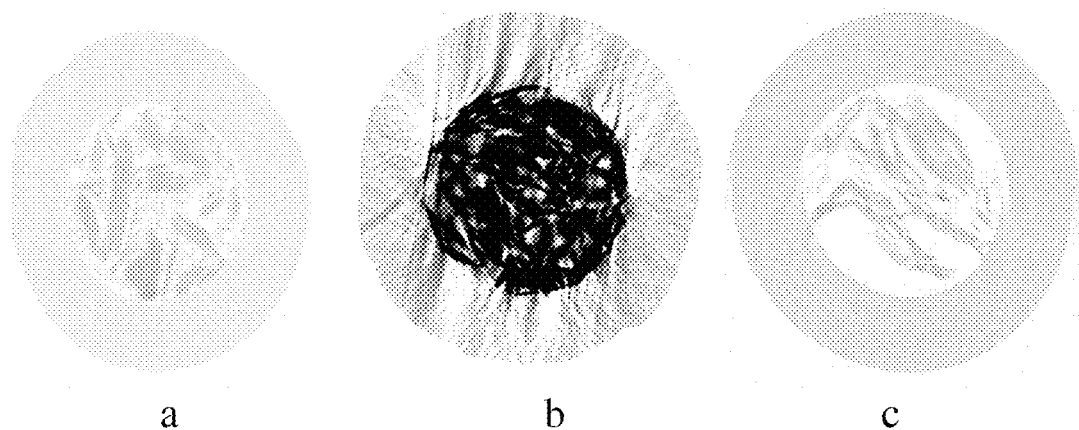

FIG. 24 shows a micro CT images of (a) empty US-tubes, (b) $I_2$-US-tubes, and (c) Na°/THF reduced $I_2$-US-tubes. The calculated radiodensities are 4366 HU, 43,716 HU, and 4395 HU respectively.

Figure 25:
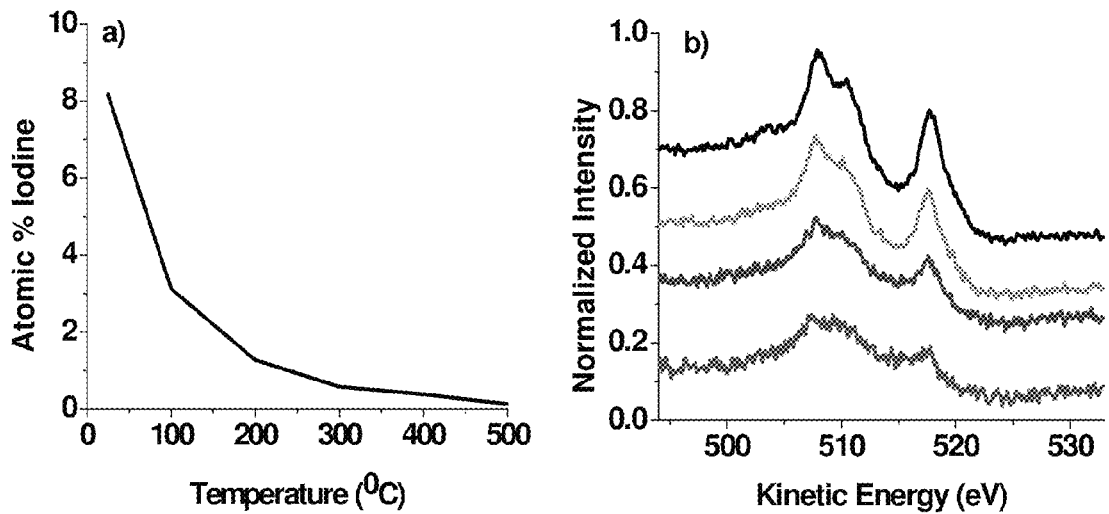

FIG. 25 shows a) Variable-temperature XPS study of $I_2$-US-tubes under high vacuum and b) X-ray induced Auger emission spectrum of $I_2$-US-tubes at room temperature (black), at 100° C. (green), at 200° C. (blue), and at 300° C. (red). All spectra were acquired under high vacuum. Possible instrument error is ±10° C. and ±0.1% iodine.

Figure 26:
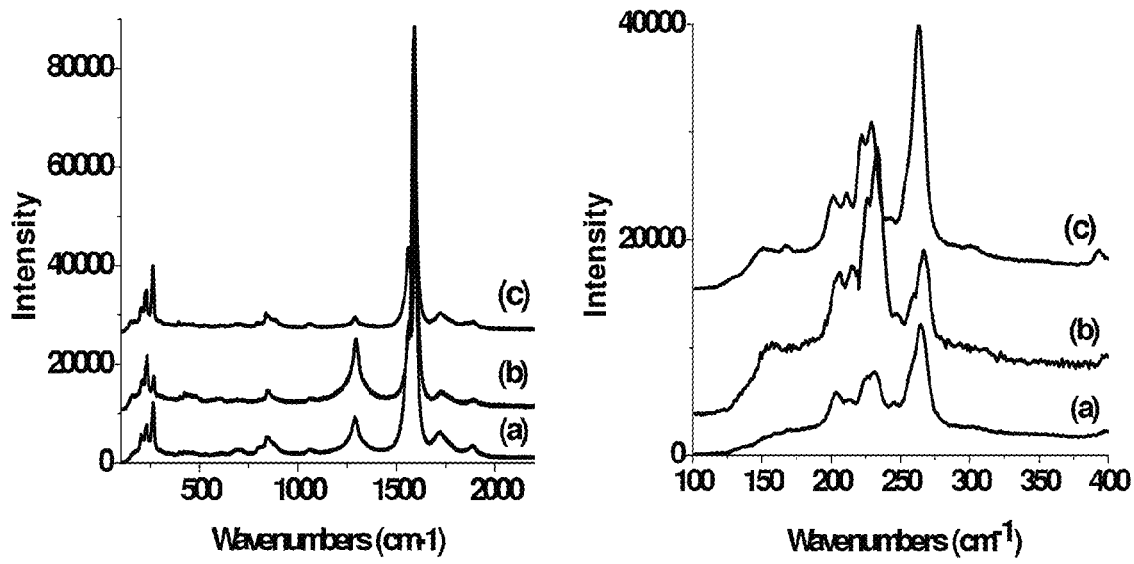

FIG. 26 shows a Raman spectrum of (a) Na°/THF reduced $I_2$-US-tubes, (b) NaH reduced $I_2$@US-tubes, and (c) Na°/THF reduced $I_2$@SWNTs. The region of interest is enlarged in the right image.

Figure 27:
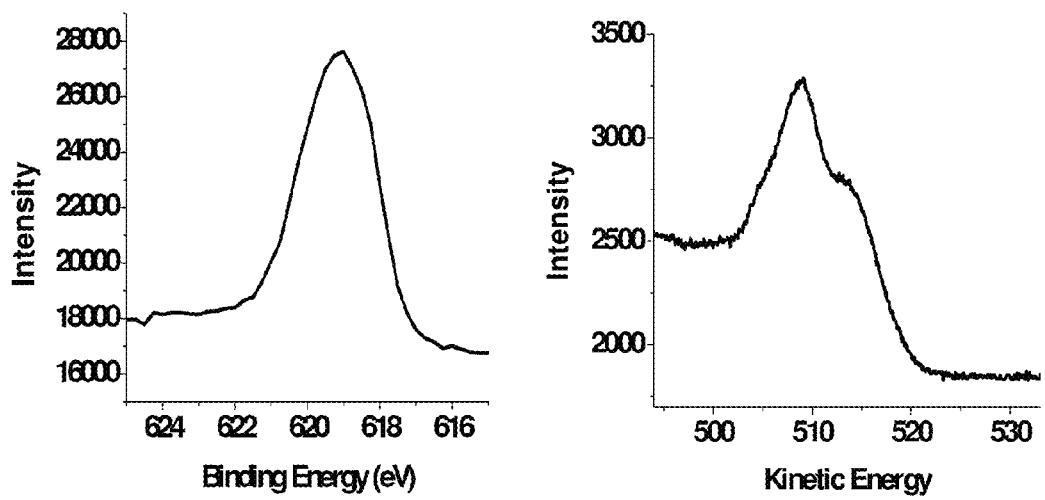

FIG. 27 shows an I $3d_{5/2}$ XPS spectrum (left) and X-ray induced Auger emission spectrum (right) of NaH reduced $I_2$@US-tubes.

Figure 28:
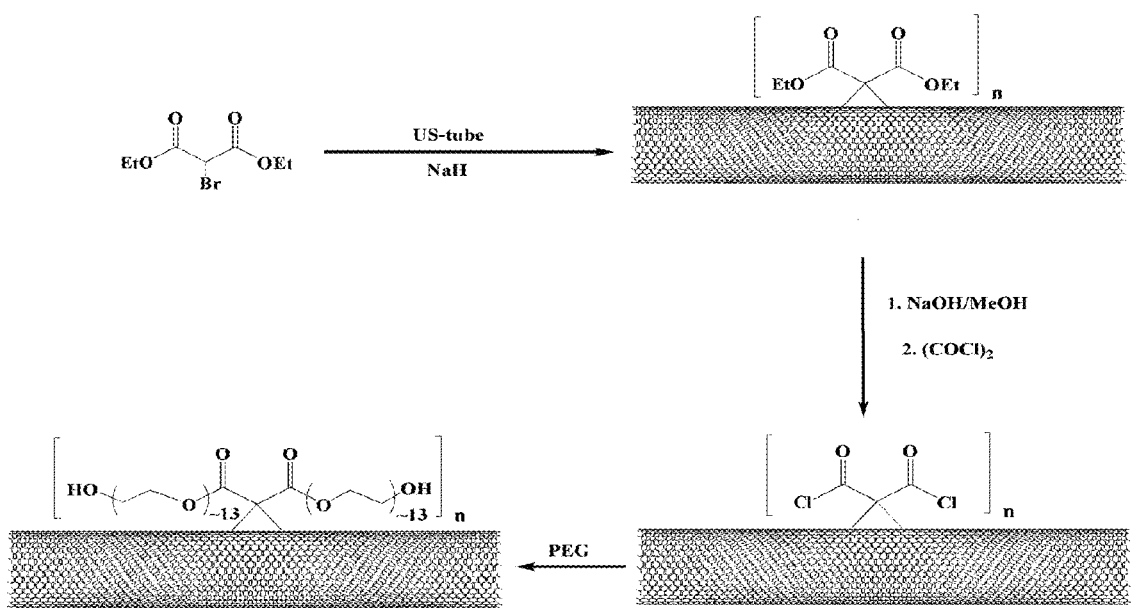

FIG. 28 shows a reaction scheme for the synthesis of PEG-US-tubes.

Figure 29:
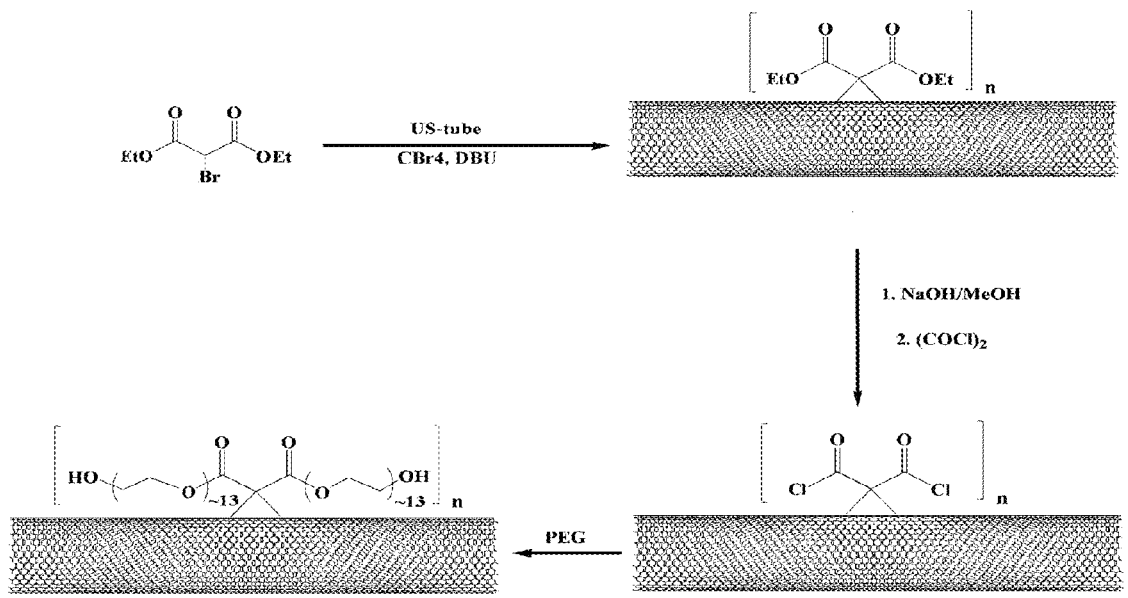

FIG. 29 shows an alternative reaction scheme for PEG-US-tubes.

Figure 30:
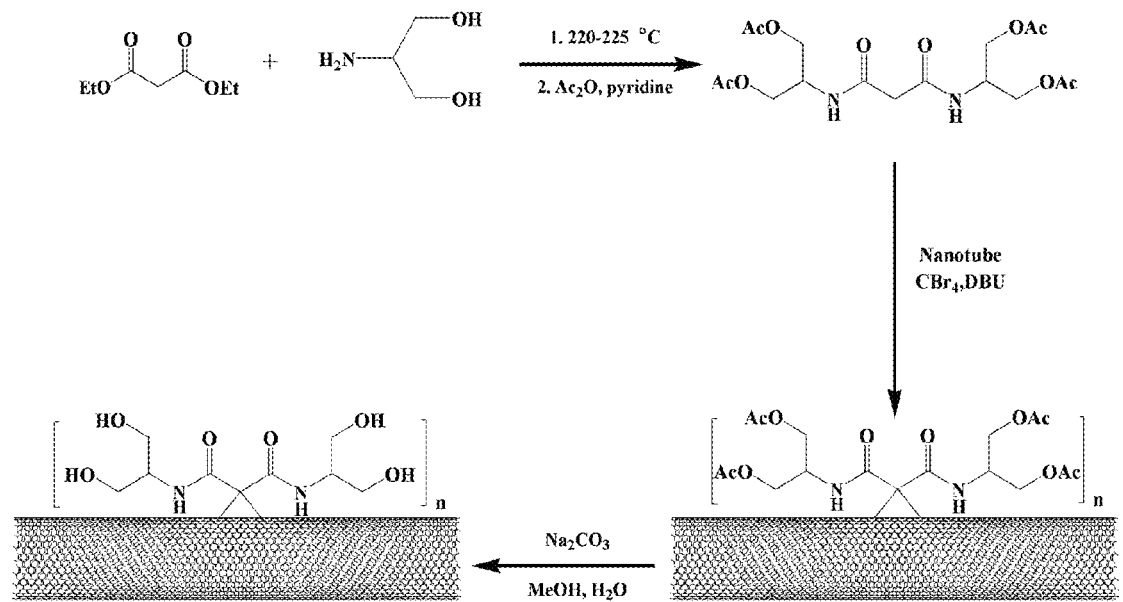

FIG. 30 shows a reaction scheme for serinol amide-US-tubes.

Figure 31:
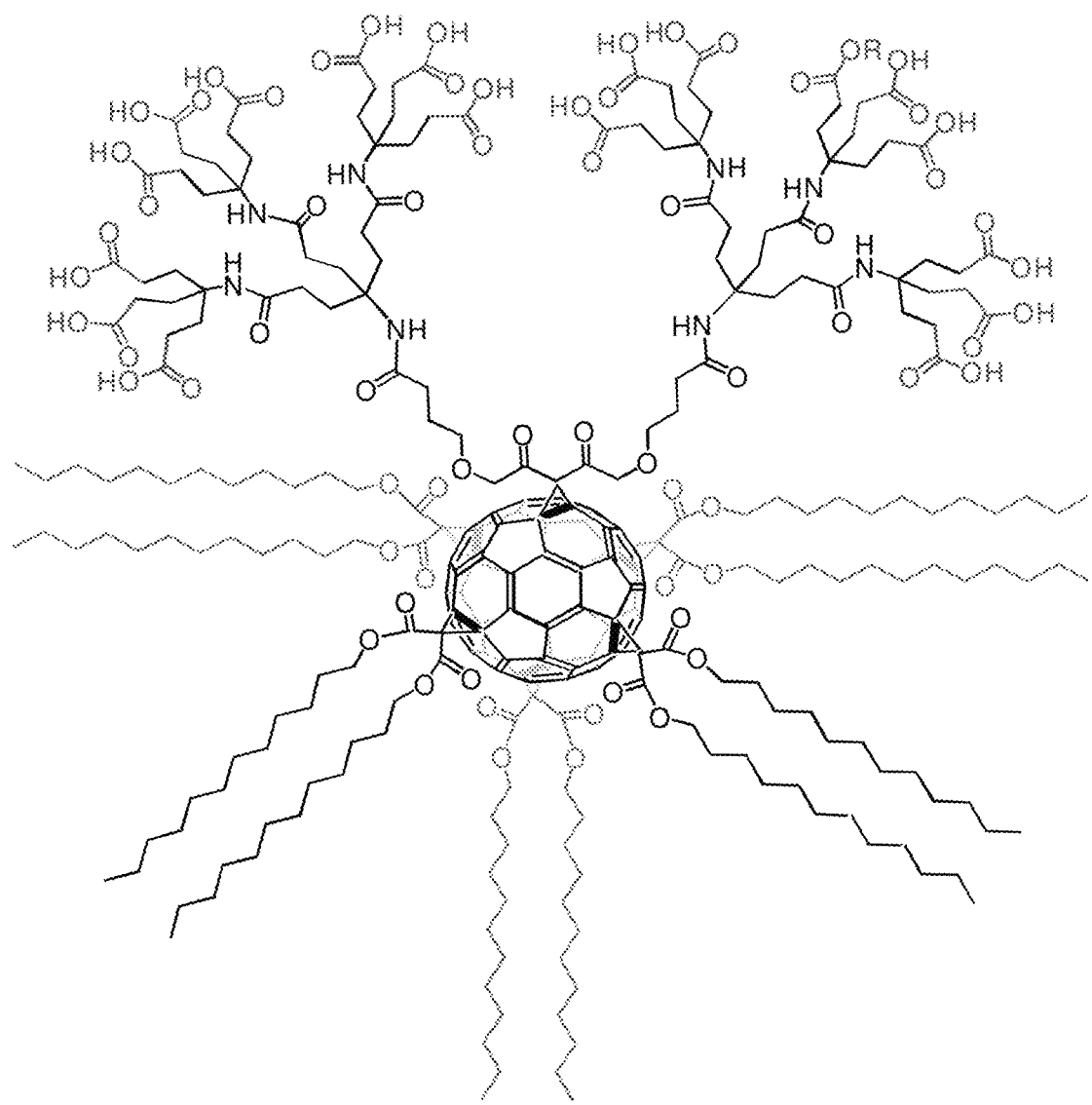

FIG. 31 shows molecular structure of amphifullerene, AF1.

Figure 32:
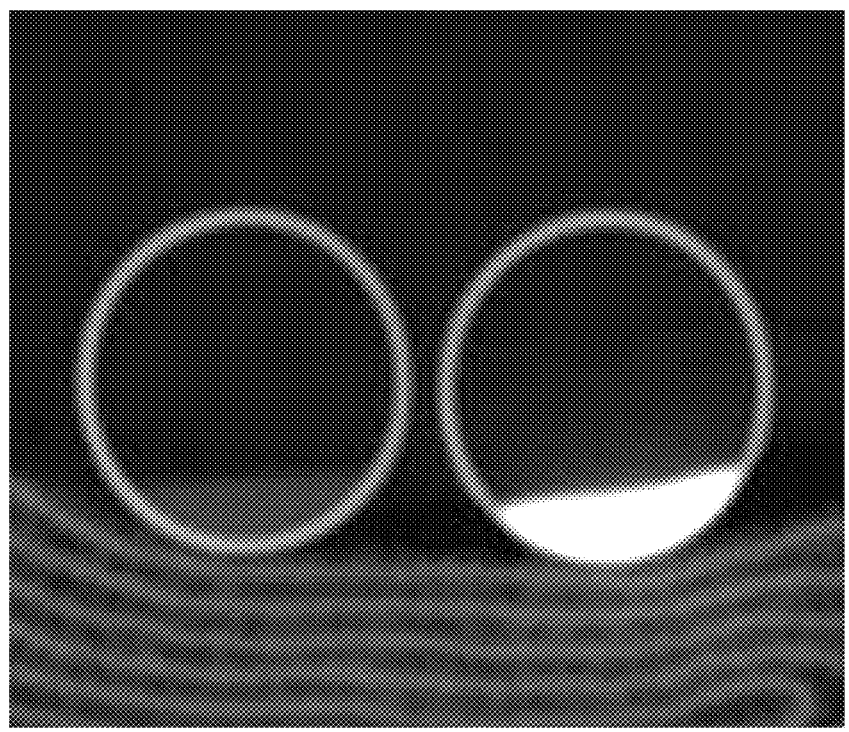

FIG. 32 shows CT image of 50 mg of unloaded SWNTs (left) and an equal amount of $I_2$ @SWNTs (right) as solids. The lines beneath the samples are a support material for the sample holders.

Figure 33:
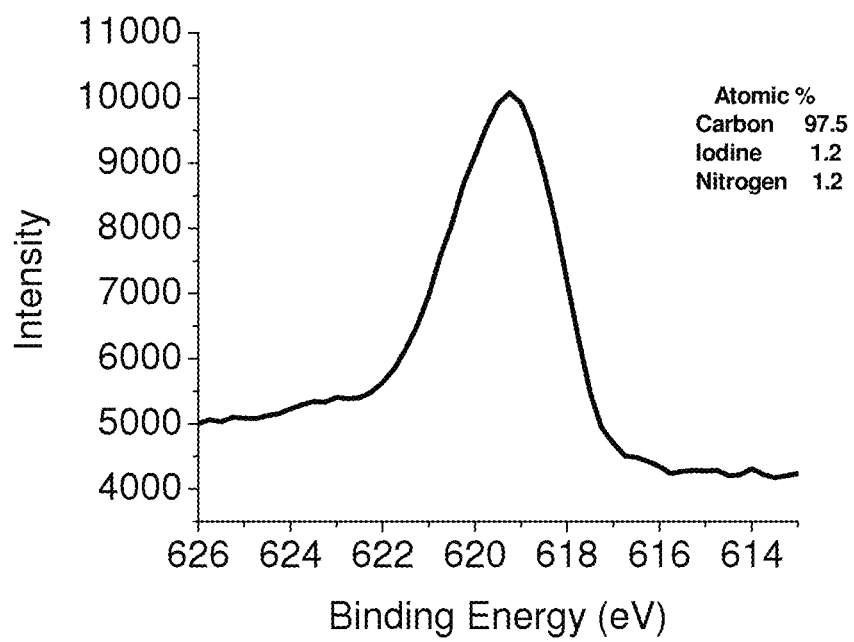

FIG. 33 shows an I 3d5/2 XPS spectrum of $I_2$ loaded US-tubes substituted with serinol after NaH reduction. The position of the peak is 619 eV, consistent with all previous measurements.

Figure 34:
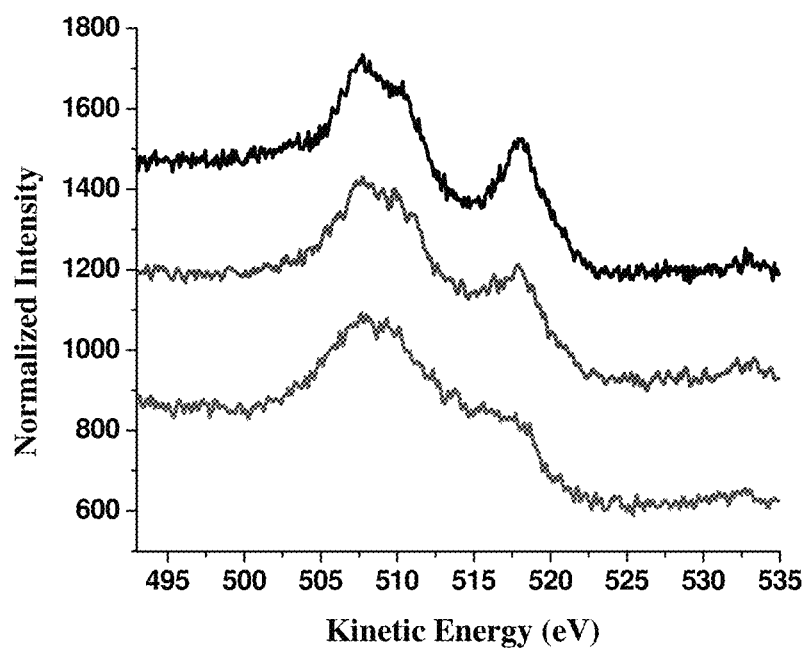

FIG. 34 shows an XAES spectrum of $I_2$ loaded US-tube substituted with serinol (black), $I_2$ loaded US-tube substituted with serinol after EtOH washing (blue), and $I_2$ loaded US-tube substituted with serinol after 10 mins NaH reduction (red). The black and blue spectra have all 3 $I_2$ peaks, meaning they contain both internal and external $I_2$. Only after the NaH reduction is all external $I_2$ removed.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure relates to compositions and methods related to carbon nanotubes. More particularly, the present disclosure relates to an imaging agent comprising carbon nanotubes internally loaded with a contrast agent and associated methods of preparation and use.

In one embodiment, the present disclosure relates to imaging agents comprising a carbon nanotube and a contrast agent. As used herein, the term "contrast agent" refers to any agent which is detectable by any means. As used herein, the term "carbon nanotube" refers to a type of fullerene having an elongated, tube-like shape of fused five-membered and six-membered rings that is approximately 1 nm in diameter. Examples of carbon nanotubes that may be used in conjunction with the methods of the present disclosure include, but are not limited to, single walled carbon nanotubes (SWNTs) and ultra-short carbon nanotubes (US-tubes).

SWNTs, also known as single walled tubular fullerenes, are cylindrical molecules consisting essentially of $sp^2$ hybridized carbons. In defining the size and conformation of single-walled carbon nanotubes, the system of nomenclature described by Dresselhaus et al., *Science of Fullerenes and Carbon Nanotubes*, Ch. 19, ibid. will be used. Single walled tubular fullerenes are distinguished from each other by a double index (x,y), where x and y are integers that describe how to cut a single strip of hexagonal graphite such that its edges join seamlessly when the strip is wrapped onto the surface of a cylinder. When x=y, the resultant tube is said to be of the "arm-chair" or (x,x) type, since when the tube is cut perpendicularly to the tube axis, only the sides of the hexagons are exposed and their pattern around the periphery of the tube edge resembles the arm and seat of an arm chair repeated n times. When y=0, the resultant tube is said to be of the "zig-zag" or (x,0) type, since when the tube is cut perpendicular to the tube axis, the edge is a zig zag pattern. Where x≠y and y≠0, the resulting tube has chirality. The electronic properties of the nanotube are dependent on the conformation, for example, arm-chair tubes are metallic and have extremely high electrical conductivity. Other tube types are metallic, semi-metals or semi-conductors, depending on their conformation. Regardless of tube type, all SWNTs have extremely high thermal conductivity and tensile strength. The SWNT may be a cylinder with two open ends, a cylinder with one closed end, or a cylinder with two closed ends. Generally, an end of an SWNT can be closed by a hemifullerene, e.g. a (10,10) carbon nanotube can be closed by a 30-carbon hemifullerene. If the SWNT has one or two open ends, the open ends can have any valences unfilled by carbon-carbon bonds within the single wall carbon nanotube filled by bonds with hydrogen, hydroxyl groups, carboxyl groups, or other groups. SWNTs can also be cut into ultra-short pieces, thereby forming US-tubes. As used herein, the term "US tubes" refers to ultra short carbon nanotubes with lengths from about 20 nm to about 100 nm.

Generally, the carbon nanotubes, more particularly, the SWNTs may be produced by the HiPco process or by electric arc discharge. Virtually all previous research about loading SWNT samples was performed with electric-arc discharge-produced SWNTs as opposed to other SWNT production methods, such as high-pressure carbon monoxide (HiPco), because arc-produced SWNTs have a larger diameter than HiPco SWNTs (1.4 nm average diameter for arc vs. 1.0 nm diameter for HiPco) and arc SWNTs are generally believed to contain more sidewall defects than HiPco SWNTs, thereby facilitating loading. For medical applications, however, the uniformity and purity of HiPco SWNTs is advantageous. Suitable commercially available carbon nanotubes may be obtained from Carbon Nanotechnologies Inc., Houston, Tex.

Current methods known in the art to produce US tubes from SWNTs require full-length SWNTs to be cut into short pieces by a four-step process. First, residual iron catalyst particles are removed by oxidation via exposure to wet-air or $SF_6$ followed by a strong acid (HCl) treatment to extract the oxidized iron particles. The purified SWNTs are then fluorinated by a gaseous mixture of 1% $F_2$ in He at elevated temperatures for up to 2 hours and cut into short pieces by pyrolysis under argon at 900° C. The fluorination reaction produces F-SWNTs, with a stoichiometry of $CF_x$ (x<0.2), which consist of bands of flurorinated-SWNT separated by regions of pristine SWNT. Pyrolysis under Ar liberates volatile fluorocarbons, thereby cutting the SWNTs into pieces with lengths corresponding to the areas of pristine SWNT. While this method known in the art is effective at producing cut SWNTs, improvements can be made; specifically, the separate purification step is unnecessary and can be eliminated.

To overcome the inefficiencies of current methods to produce US tubes, a three-step process may be used to produce US tubes. First, as produced HiPco SWNTs are fluorinated in a monel steel apparatus by a mixture of 1% $F_2$ in He at 100° C. for 2 hours. During this process, both the SWNTs and the iron catalyst particles become fluorinated. Subsequent exposure to concentrated HCl removes the fluorinated catalyst particles without affecting the F-SWNTs, which have a stoichiometry of ~$C_{10}F$ after the acid treatment. The, now-purified, F-SWNTs are cut into US-tubes by pyrolysis under Ar at 900° C. The resulting US-tubes have lengths ranging from 20-80 nm, with the majority being ~40 nm in length. Utilizing this method, the amount of iron catalyst is reduced from ~25 mass percent in raw SWNTs to ~1 mass percent for US-tubes. Therefore, this method is ideal for the purification of SWNTs, but only as a precursor to producing US-tubes. This is because the fluorine remaining, after the HCl acid treatment, is very hard to remove, making the F-SWNTs only viable for subsequent cutting. Furthermore, the time to produce US tubes from SWNTs using this method is significantly reduced.

Typically, carbon nanotubes are of micron-length. Such lengths may reduce the ability of the carbon nanotubes to internalize into the cells. The carbon nanotubes of the present disclosure may be of a length of about 100 nm to about 5 μm, alternatively 100 nm or less, alternatively of about 50 nm or less, and alternatively from about 20 nm to about 50 nm. Generally, carbon nanotubes of nano-length may be suited for internalization by cells. In certain embodiments, the carbon nanotubes used in the compositions of the present disclosure may comprise US tubes of length in the range of about 20 nm to about 80 nm. In certain embodiments, the carbon nanotubes used in the compositions of the present disclosure may comprise SWNTs of a length of less than 100 nm.

The carbon nanotube can be substituted or unsubstituted. By "substituted" it is meant that a group of one or more atoms is covalently linked to one or more atoms of the carbon nanotube. Generally, Bingel chemistry may be used to substitute the nanotube with appropriate groups. Examples of groups suitable for use include, but are not limited to, malonate groups, serinol malonates, groups derived from malonates, serinol groups, serinol amide, carboxylic acid, dicarboxyilic acid, polyethyleneglycol (PEG), and the like. In certain embodiments, the carbon nanotube is substituted with one or more water-solubilizing groups. Water-solubilizing groups are polar groups (that is, groups having a net dipole moment) that render the generally hydrophobic nanotube soluble in water. Such groups may allow for greater biocompatibility of the carbon nanotube and enhanced diffusion through the cell membrane. In certain embodiments, the carbon nanotube may be substituted before loading of the contrast agent within the tube. For example, in certain embodiments using US tubes, the US tubes may be substituted with serinol groups prior to loading of a contrast agent within the tube. The degree of lipophilicity of the substituted nanotube should roughly parallel the degree of lipophilicity of the groups covalently linked to the surface of the nanotube.

The imaging agents of the present disclosure also comprise a contrast agent. In certain embodiments, the contrast agent is $I_2$. In other embodiments, the contrast agent may be any iodine moiety. In other embodiments, the contrast agent may be magnetic metallic particles, such as $Gd^{3+}$. Examples of contrast agents include, but are not limited to, MRI contrast agents (e.g. magnetic metal particles), CT contrast agents (e.g. hyperpolarized gas), X-ray contrast agents, nucleosan contrast agents, and ultrasonic contrast agents, among others.

The contrast agents of the present disclosure are generally sequestered within the carbon nanotube. Generally all or a portion of the carbon nanotube may be loaded with contrast agent. The carbon nanotubes may be loaded through the ends of the carbon nanotubes and/or through the side wall defects. Examples of suitable methods that may be used to load the carbon nanotubes with contrast agent include, but are not limited to, solution phase method, molten phase method, and sublimation. One of ordinary skill in the art, with the benefit of the disclosure will realize what method would be suitable for loading the carbon nanotube based on the properties of the contrast agent to be loaded.

To prepare the imaging agents of the present invention, loading by sublimation may be effective when using materials that sublime at relatively low temperatures, such as $I_2$. In certain embodiments, carbon nanotubes are loaded with $I_2$ in high yields via sublimation. In certain embodiments, HiPco SWNTs are loaded with a contrast agent, such as $I_2$. Typically, HiPco SWNTs are not used for loading experiments because the interior of the HiPco SWNT was thought to be inaccessible for loading due to the lack of sidewall defects and the presence of the iron catalyst particle, which blocks the open end of the SWNT. However, such HiPco produced tubes do load with $I_2$ without exposure to strong acids, known to create sidewall defects in the nanotube that would facilitate loading. It may be possible for $I_2$ to react with the iron catalyst particle to remove it from the end of the SWNT, thus allowing loading through the open end of the SWNT. US tubes may also be loaded in the same manner as SWNTs.

Though the nanotubes are able to be loaded, exterior adsorbed $I_2$ must be removed. In certain embodiments, a chemical reduction procedure may be performed to debundle carbon nanotubes after loading with the contrast agent to ensure that the contrast agent is completely sequestered within the carbon nanotubes. In particular, procedures useful for debundling SWNTs are known in the art. One such procedure, a $Na^0$/THF reduction reaction, results in the SWNTs becoming highly charged (~10 electrons/nm), which creates an electrostatic repulsion resulting in the debundling of the nanotubes into mostly individual SWNTs. In the case of $I_2$ loaded SWNTs, this debundling would allow for any $I_2$ intercalated within the surface spaces of a SWNT bundle to be chemically reduced to $I^-$ and washed away. In other embodiments, the $I_2$ loaded SWNTs may be heated to 300° C. without reduction to remove $I_2$ adsorbed to the exterior surface of the nanotube. In these embodiments, the resulting loaded nanotubes are stable and loaded contrast agent will not be lost even after further reduction steps or additional heating.

In certain embodiments, the carbon nanotubes are US tubes and such reduction methods for SWNTs result in the unloading of contrast agent, $I_2$, from the interior of the US tubes. In these embodiments, the US tubes may be reduced using NaH. Such reduction methods, however, are time-dependent. The length the reaction is allowed to proceed will depend on the presence or absence of internally loaded $I_2$. Generally, in these embodiments, when reduction reactions are performed on carbon nanotubes loaded with contrast agents, the reaction should not proceed for longer than one hour to ensure that contrast agent remains loaded within the tubes. In other embodiments, the removal of externally adsorbed $I_2$ may occur by heating the loaded nanotubes to 400° C.

In certain other embodiments, the imaging agents of the present disclosure may comprise carbon nanotubes that are US tubes. In these embodiments, the US tubes may be substituted with serinol groups prior to loading with contrast agent. The contrast agent may be $I_2$ and may be loaded after the US tubes have been substituted via sublimation. To remove the any exterior adsorbed contrast agent, the US tubes may be reduced using NaH to form a substituted and loaded US tube imaging agent.

In certain embodiments, the imaging agents of the present disclosure may be enclosed within a buckysome. As used herein, the term "buckysome" refers to amphifullerenes, AF1, (FIG. 31) that have self assembled into unilamellar vesicles which resemble unilamellar liposomes. As used herein, the term "unilamellar" refers to having only one bilayer around an aqueous core. The imaging agents of the present disclosure may be entrapped within the fullerene cage of the buckysome. Buckysomes have been found to be temperature and pH sensitive. In certain embodiments, under high temperature and pH, the imaging agents may be released at much higher rates than at low temperature and low pH. This pH dependent release is due to the protonation and deprotonation of the carboxylic acid groups of the individual AF1 groups. Upon deprotonation, the carboxylic acid moieties become negatively charged and may repel one another, resulting in a more fluid structure which increases the release of imaging agent from the vesicles. An acidic environment results in a more tightly packed structure. Additionally, the AF1 molecule has potential for an almost unlimited degree of further derivatization of its structure, which gives it "tunability" with respect to imaging agent release.

In certain embodiments, the imaging agents of the present disclosure may be used to diagnose diseases. Examples of such diseases include, but are not limited to, coronary heart disease resulting from vulnerable plaque, intracranial hemorrhages, acute and chronic lung conditions such as cancer, emphysema, or pneumonia, and several abdominal conditions such as kidney stones or appendicitis. In these embodiments, the imaging agents may be internalized by cells of interest. Imaging techniques known in the art may be used to detect the presence of imaging agent after internalization by the cells. Such imaging techniques include, but are not limited to, CT, MRI, X-Ray, and the like.

To facilitate a better understanding of the present disclosure, the following examples of certain aspects of some embodiments are given. In no way should the following examples be read to limit, or define, the entire scope of the invention.

EXAMPLES

Example 1

Synthesis of $I_2$ Loaded SWNTs (Hereinafter $I_2$-SWNTs)

Figure 1:
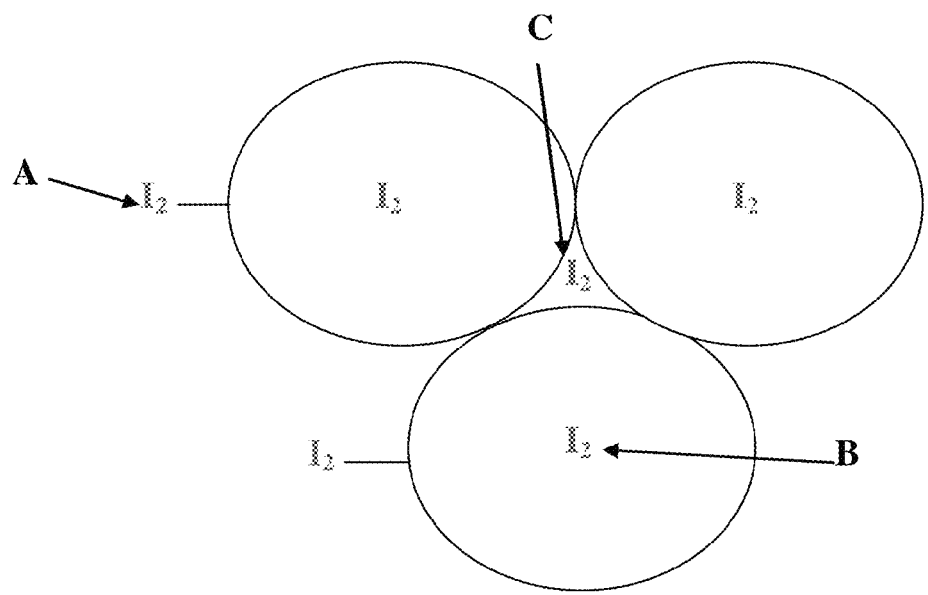
FIG. 1 shows the three species of $I_2$ present in $I_2$-loaded full-length SWNTs: (A) physisorbed to the outside of a nanotube bundle, (B) contained within the interior of the nanotube, and (C) intercalated within the interstitial spaces of a nanotube bundle.

A raw nanotube sample of SWNTs, produced by the HiPco process, with an average diameter of 1.0 nm and containing ~25% by weight iron catalyst impurities was obtained from Carbon Nanotechnologies Inc. The, as received, SWNT sample was not purified by exposure to a strong acid treatment which is known to create additional defects in the sidewalls. Loading of raw, full-length SWNTs with contrast agent, $I_2$ was accomplished via sublimation of $I_2$ (~100° C.) in the presence of SWNTs for one hour in a closed glass vessel. In all cases, SWNTs and $I_2$ were kept separate to ensure loading was via $I_2$ sublimation and not via molten iodine. In a typical experiment, 50 mg of raw SWNTs were used and the SWNT sample gained approximately 80% mass during the loading process (total mass after loading was ~90 mg). However, not all of this mass gain is due to internally-loaded $I_2$; in fact, a central question surrounding loaded SWNTs is whether the loading material is contained within the interior of the SWNT or adsorbed to its exterior surface. Nanotubes aggregate into large bundles which are difficult to separate (~1 eV/nm binding energy) and hydrophobic molecules, e.g. $I_2$, can become intercalated in the surface spaces within a SWNT bundle. As shown in FIG. 1, there are actually 3 possible $I_2$ species present; $I_2$ adsorbed to the exterior of a nanotube bundle, $I_2$ intercalated within the surface spaces of a nanotube bundle, but not loaded within any one SWNT, and $I_2$ loaded within the interior of a SWNT.

Example 2

Thermal Gravimetric Analysis of $I_2$-SWNTs

Figure 2:
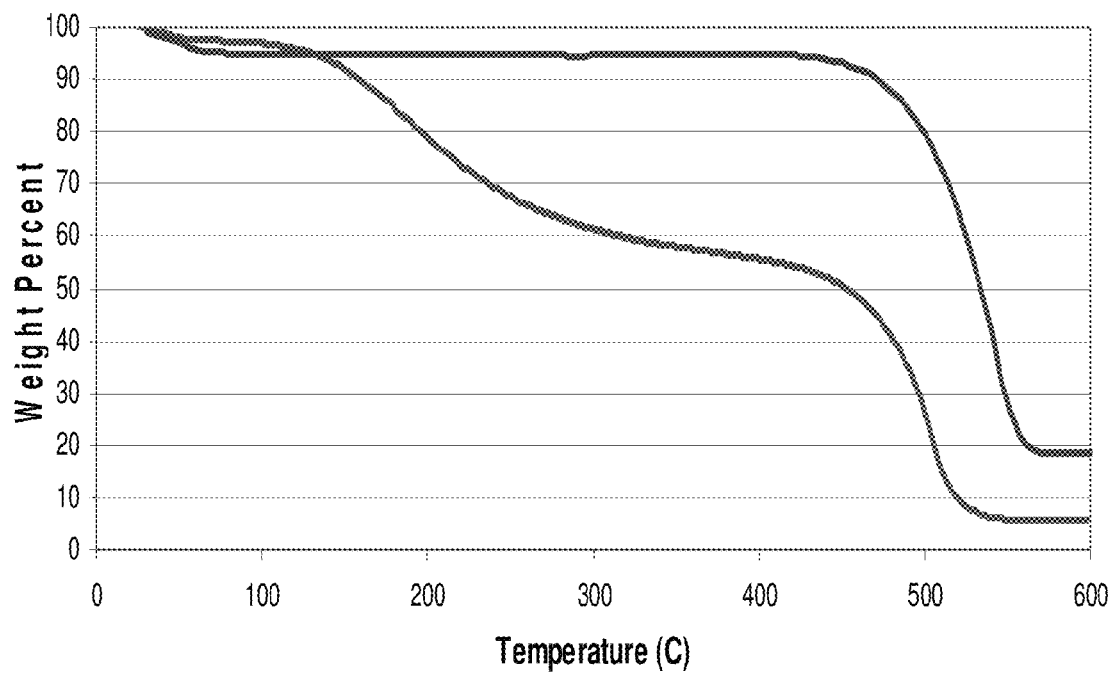
FIG. 2 shows thermal gravimetric analysis of raw SWNTs (blue) and $I_2$-SWNTs (red).

Thermal gravimetric analysis (TGA) in air measures the mass loss of the $I_2$-SWNTs as a function of temperature (FIG. 2). Raw SWNTs, with no loaded $I_2$, exhibit very little loss of mass until temperatures greater than 400° C. are reached, at which point the SWNTs combust. For $I_2$-SWNTs, mass loss is observed much earlier, around 150° C., as $I_2$ is liberated. The total mass lost from 150° C. to 400° C., when the SWNTs again combust, is approximately 35%, which is in good agreement with the observed mass gain from the loading process. However, no distinction can be made as to which species of $I_2$ is liberated and only a quantification of the total amount of iodine removed can be made. For raw SWNTs, the mass remaining at 600° C. is iron oxide residue from iron catalyst particles present in raw SWNTs; 19 mass percent of iron oxide remaining corresponds to an initial iron content of 25% by mass. In the case of the $I_2$-SWNTs, only 7 mass percent remains at 600° C. This is not necessarily because iron is being removed during the loading process. The added iodine mass due to the loading process results in a lower overall mass percent of iron in the $I_2$-SWNTs.

Example 3

Raman Spectroscopy of $I_2$-SWNTs

Figure 3:
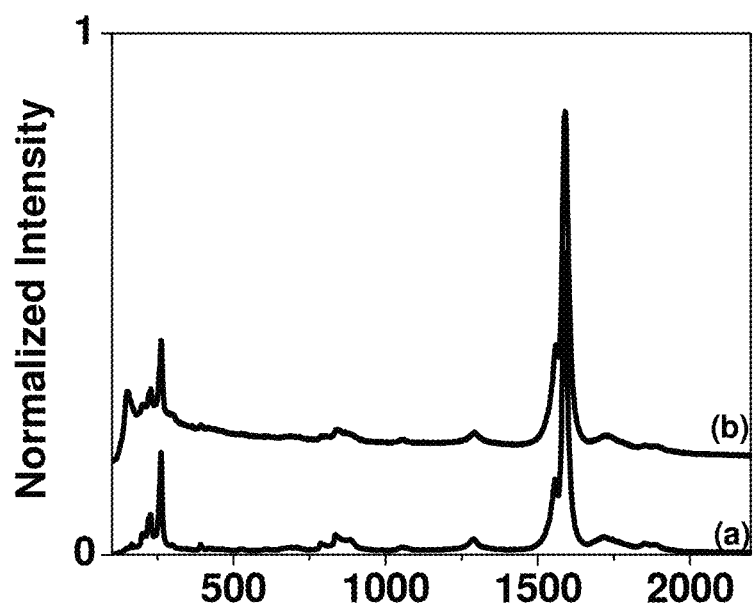
FIG. 3 shows a Raman spectrum of (a) raw SWNTs and (b) $I_2$-SWNTs.

Raman spectroscopy provides additional structural information about the $I_2$-SWNTs but is also unable to distinguish the multiple species of $I_2$ present. Comparative Raman spectra of raw SWNTs and $I_2$-SWNTs are shown in FIG. 3. Characteristic SWNT bands at 1590 cm$^{-1}$ (sp$^2$ hybridized carbon), 1350 cm$^{-1}$ (sp$^3$ hybridized carbon), and in the region of 100-300 cm$^{-1}$ (radial breathing modes for SWNTs of various diameters) are present in both the raw SWNT and $I_2$-SWNT samples. However, the $I_2$-SWNTs exhibit an additional band at 159 cm$^{-1}$ which is not present in the raw SWNT spectrum. This peak disappears when the $I_2$-SWNTs are heated to 1000° C. and reappears after a second $I_2$ sublimation treatment, therefore it can confidently be assigned to the ν(I-I) stretching mode. The position of this ν(I-I) band for $I_2$-SWNTs, 159 cm$^{-1}$, is somewhat surprising, because it does not correspond with either the ν(I-I) stretching mode observed at 178 cm$^{-1}$ for crystalline $I_2$ or at 211 cm$^{-1}$ for gaseous $I_2$. Thus, the interior of a SWNT or SWNT bundle is a unique chemical environment. While this is interesting information, Raman spectroscopy alone is not able to identify or quantify the multiple species of $I_2$ present; thus other techniques, such as electron microscopy, must be explored.

Example 4

Transmission Electron Microscopy of $I_2$-SWNTs

Figure 4:
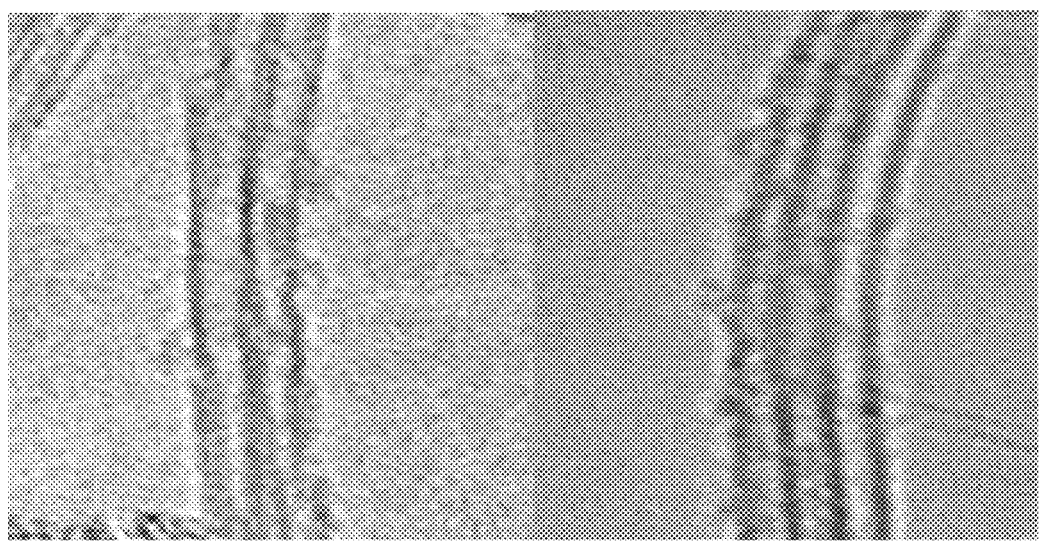
FIG. 4 is a TEM image of raw SWNTs (left) and $I_2$-SWNTs (right).

High-resolution transmission electron microscopy (HR-TEM) has thus far been the method of choice for characterizing loaded SWNT samples. While HRTEM is a powerful technique and is able to visualize individual atoms of loading material, HRTEM does have several disadvantages. The long acquisition time, inability to characterize bulk samples, and inability to quantify each species present of HRTEM indicate that better techniques are needed for complete characterization. Perhaps the greatest disadvantage of the HRTEM used in the previous work is its uniqueness; very few labs in the world have the equipment and software necessary to perform this type of HRTEM analysis. Due to the limited availability of the equipment, only regular TEM could be performed on the $I_2$-SWNTs. In addition to the disadvantages experienced by HRTEM, the resolution of regular TEM is too low to visualize individual $I_2$ molecules. In fact, very little difference can be seen between raw SWNTs and $I_2$-SWNTs (FIG. 4). Energy Dispersive X-ray spectroscopy (EDAX) does confirm the presence of iodine loaded in the $I_2$-SWNTs and the absence of iodine in raw SWNTs, but certainly this method cannot be used to identify or quantify the multiple species of $I_2$ present.

Example 4

X-ray Photoelectron Spectroscopy of $I_2$-SWNTs

Figure 5:
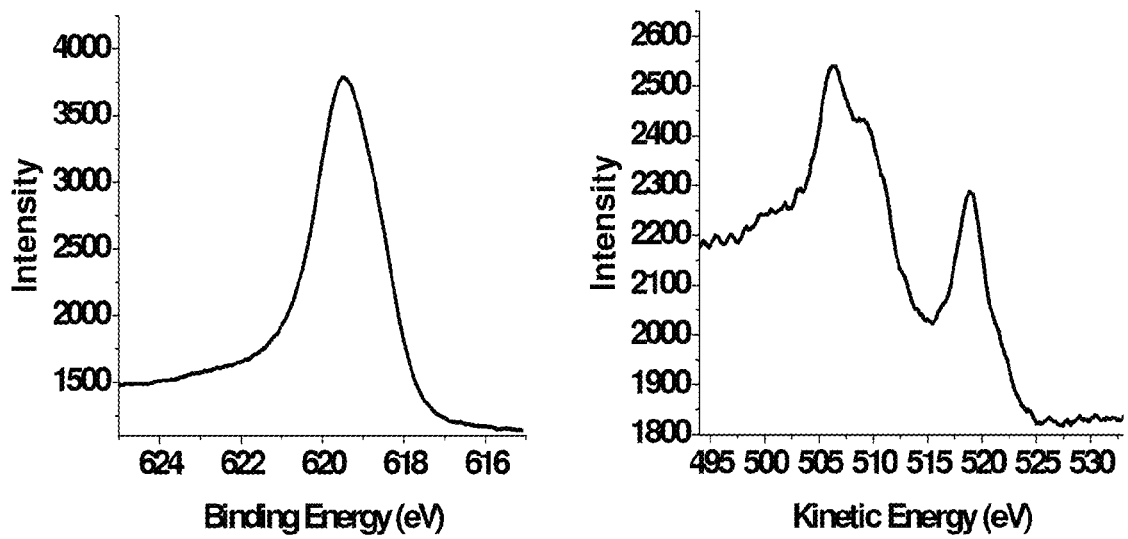
FIG. 5 shows an I $3d_{5/2}$ XPS spectrum (left) and X-ray induced Auger emission spectrum (right) of $I_2$-SWNTs.
Figure 6:
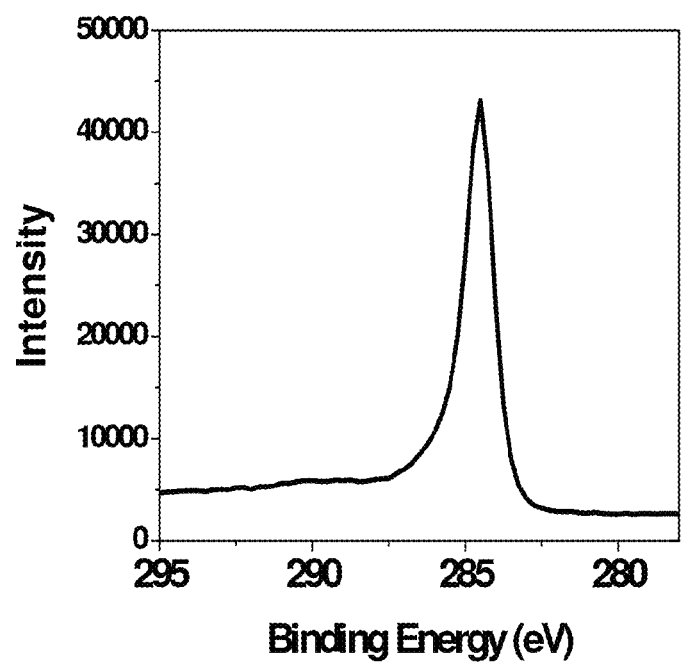
FIG. 6 shows a C is XPS spectrum for $I_2$-SWNTs

After loading, the $I_2$-SWNTs contained 5.3 atomic % of iodine by XPS (36% by mass) which agrees well with the mass gain observed during the loading process. The position of the I-3d$_{5/2}$ peak in the XPS spectrum (FIG. 5) at 619.5±0.2 eV is consistent with accepted values for $I_2$ (as opposed to polyiodide chains such as $I_3^-$ and $I_5^-$), indicating that $I_2$ does not react with SWNTs to form C—I bonds. This is also confirmed by the absence of a second peak in the C is spectrum (FIG. 6), which would also indicate C—I bond formation, for the $I_2$-SWNT sample. However, only one peak is observed in the I-3d$_{5/2}$ region and no shoulders are visible which would indicate the presence of a hidden second peak. Therefore, it would appear that XPS cannot distinguish between the $I_2$ species. However, inspection of the X-ray-induced Auger emissions reveals several features of interest (FIG. 5). For $I_2$-SWNTs, the X-ray induced Auger emission spectrum exhibits peaks at kinetic energies of 507.5±0.2 eV and 519.0±0.2 eV. Additionally, there is a prominent shoulder observed on the 507.5 eV peak, with a maximum at ~510 eV. The 507.5 and 510.0 eV peaks stem from I-M$_5$N$_{45}$N$_{45}$ emissions, whereas the 519.0 peak stems from I-M$_4$N$_{45}$N$_{45}$ emissions. Unfortunately, despite lengthy efforts curve-fitting the various peaks in the X-ray induced Auger emission spectrum; no conclusive discrimination of individual $I_2$ species could be made. It became obvious that the only method to definitively identify any single $I_2$ species was to debundle the SWNTs; this would result in the intercalated $I_2$ becoming accessible to an organic solvent or a reactive species, leading to the removal of this unwanted, external $I_2$ species.

Example 5

Chemical Reduction of SWNTs

Figure 7:
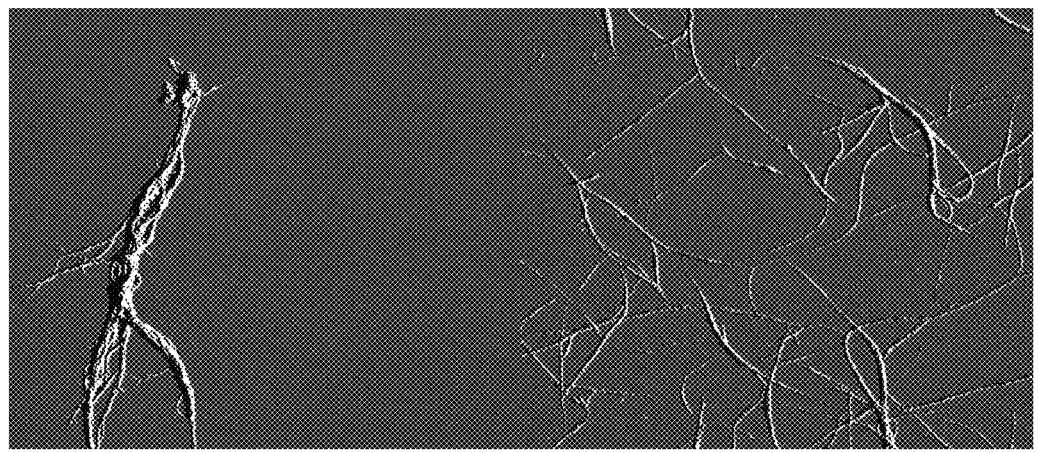
FIG. 7 shows an AFM image of raw HiPco SWNTs (left) and reduced HiPco SWNTs (right).
Figure 8:
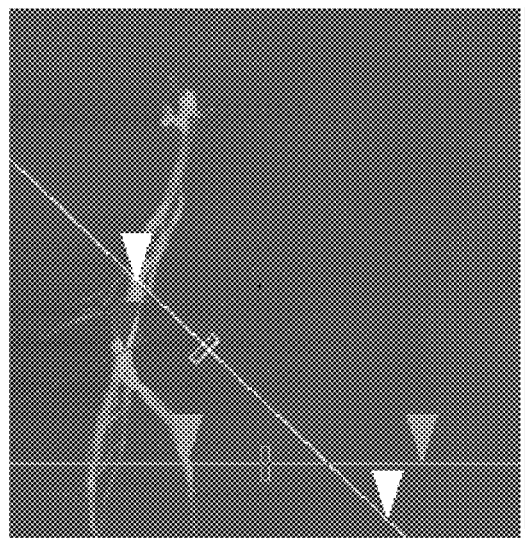
FIG. 8 shows AFM height measurements for raw HiPco SWNTs.
Figure 9:
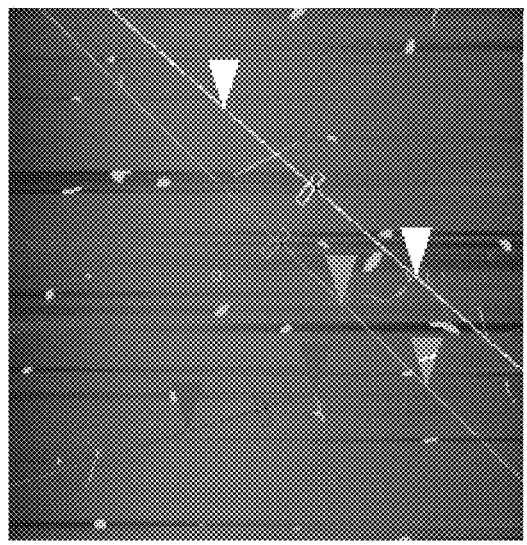
FIG. 9 shows AFM height measurements for Na°/THF reduced HiPco SWNTs.

A method of debundling SWNTs via chemical reduction in tetrahydrofuran (THF) was published by Petit et al. 50 milligrams of raw SWNTs were added to a dry 250 mL round bottom flask with a 2:1 molar excess of sodium metal (100 mg). Then, 150 mL of dry THF was added to the flask, and the flask was purged with N$_{2(g)}$, capped, and bath sonicated for one hour. After one hour, the reduction reaction was quenched with DI water and the sample was isolated using a glass frit filter (Pyrex #36060). Atomic force microscopy (AFM) confirmed the debundling of the SWNTs by the Na°/THF reduction reaction into mostly individuals (FIG. 7). The AFM image was acquired before the addition of water, although the SWNTs are likely quenched via exposure to the atmosphere. Height measurements taken for several points in the reduced SWNT sample measure ~1 nm, corroborating individual SWNTs (FIGS. 8 and 9).

Example 6

Raman Spectroscopy of Na°/THF Reduced SWNTs

Figure 10:
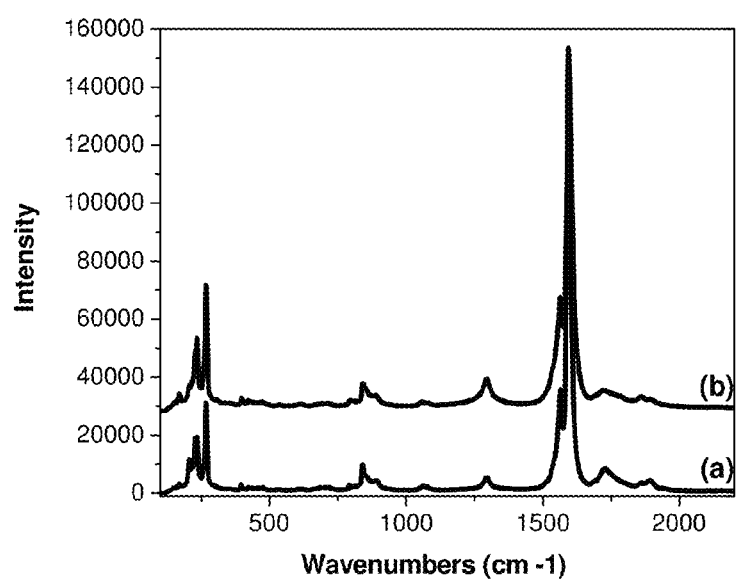
FIG. 10 shows a Raman spectrum of (a) raw HiPco SWNTs and (b) Na°/THF reduced HiPco SWNTs.

Raman spectroscopy was used to assess structural changes in the SWNTs as a result of the Na°/THF reduction reaction. Such changes could be either residual delocalized negative charge not quenched by the addition of water as suggested in the original work, or protonation (similar to the Birch reaction) of the charged SWNTs upon quenching by water. As shown in FIG. 10, the Raman spectrum before and after the Na°/THF reduction is nearly identical, with the exception of a small increase in the disorder band at ~1300 cm$^{-1}$. This band is indicative of sp$^3$-hybridized carbon which suggests that some degree of protonation of the SWNTs has occurred. This was confirmed by an elemental analysis performed by Galbraith Laboratories which showed increased hydrogen content in the Na°/THF reduced SWNTs, with a C:H ratio of ~20:1 measured for Na°/THF reduced SWNTs as opposed to a C:H ratio of >150:1 measured for raw SWNTs (Table 1). Once the effects of the Na°/THF reduction reaction on raw SWNTs were understood, a Na°/THF reduction was performed on $I_2$-SWNTs under the same reaction conditions to determine if removal of intercalated $I_2$ was achieved.

TABLE 1

Carbon and hydrogen elemental analysis of raw HiPco SWNTs and Na°/THF reduced HiPco SWNTs

| Sample | Atomic Percent | |
|---|---|---|
| | Carbon | Hydrogen |
| Raw HiPco SWNTs | 69.49 | <0.5 |
| Na°/THF reduced HiPco SWNTs | 67.91 | 3.21 |

Example 7

XPS of Na°/THF Reduced $I_2$-SWNTs

After an $I_2$-SWNT sample was reduced by the Na°/THF reaction, 2.8 atomic % or 22% by weight $I_2$ remained in the sample, which approximates to be 3.1 atoms of iodine/nm of SWNT. A slight shift of the I-$3d_{5/2}$ peak to a lower binding energy (619.1±0.2 eV) is observed in the reduced $I_2$@SWNT sample; however, the shift is within experimental error and is not large enough to provide conclusive evidence as to the removal of exterior-adsorbed $I_2$. Additionally, this value is still within those accepted for $I_2$, which indicates the remaining $I_2$ in the sample has not been reduced to some polyiodide form ($I_3^-$ or $I_5^-$) as a result of the Na°/THF reaction. This would likely occur only if the remaining $I_2$ was sequestered within the interior of the hydrophobic nanotube and therefore, inaccessible to chemical reduction.

Figure 11:
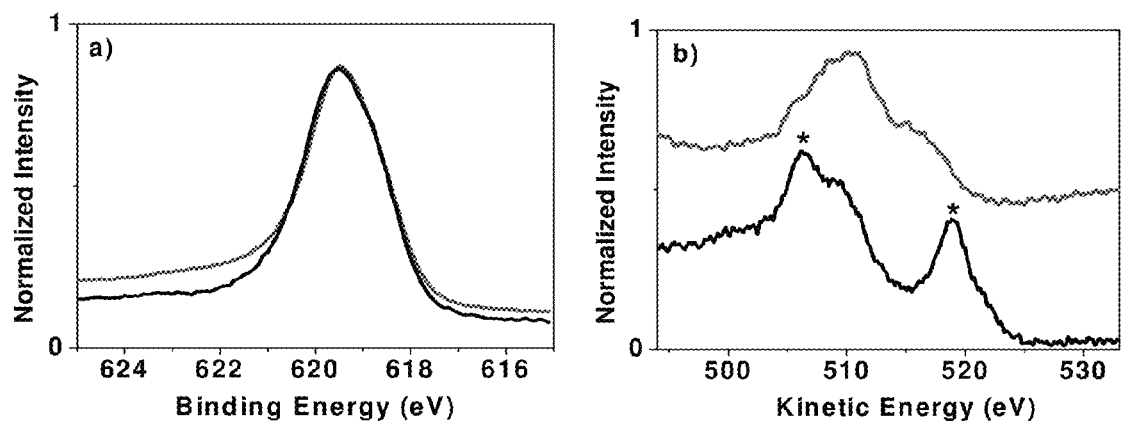
FIG. 11 shows a) I $3d_{5/2}$ XPS spectrum of $I_2$-SWNTs (black) and $I_2$@SWNTs (red) reduced by the Na°/THF reaction and then quenched by water. b) X-ray induced Auger emission spectrum over the I MNN region for $I_2$-SWNTs (black) and $I_2$@SWNTs (red) reduced by the Na°/THF reaction and then quenched by water. The peaks due to externally-adsorbed $I_2$ are denoted by an asterisk.

Inspection of the X-ray induced iodine Auger emission spectrum reveals significant differences between the $I_2$-SWNT sample and the Na°/THF reduced $I_2$@SWNTs. As described above, the unreduced $I_2$-SWNT sample exhibits peaks at kinetic energies of 507.5±0.2 eV and 519.0±0.2 eV, with a prominent shoulder observed on the 507.5 eV peak (maximum at ~510 eV). The reduced $I_2$@SWNT sample, on the other hand, exhibits a single peak at 510.0±0.2 eV with a shoulder at approximately 517 eV. This shoulder is initially hidden in the $I_2$-SWNT spectrum by the $I_2$ peak at 519 eV and is likely also due to internal $I_2$. This phenomenon is also observed in the Auger temperature studies discussed below (red trace in FIG. 12b). Representative spectra comparing the iodine photoelectron and X-ray induced Auger emissions for the $I_2$-SWNT (black) and reduced $I_2$@SWNT (red) samples are shown in FIG. 11. As discussed above, the 507.5 and 510.0 eV peaks stem from I-$M_5N_{45}N_{45}$ emissions, whereas the 519.0 peak stems from I-$M_4N_{45}N_{45}$ emissions. This allows for the calculation of Auger parameters for each peak, a valuable tool in deriving chemical state information.

Since the I-$M_4N_{45}N_{45}$ emissions appear at 11.5 eV lower kinetic energy than I-$M_5N_{45}N_{45}$ emissions, addition of this value allows for Auger parameters to be derived. Such parameters are an effective method of deriving additional chemical state information. Auger parameters are derived by adding the I-$3d_{5/2}$ peak binding energy to the I-$M_4N_{45}N_{45}$ kinetic energy, or by adding the I-$3d_{5/2}$ peak binding energy to the I-$M_5N_{45}N_{45}$ kinetic energy plus 11.5 eV. For the unreduced $I_2$-SWNT sample, Auger parameter values of 1138.5 eV for the 507.5 eV peak, 1141.0 eV for the 510.0 eV shoulder, and 1138.5 eV for the 519.0 eV peak are derived. A value of 1141.0 eV is derived for the peak at 510.0 eV in the Na°/THF reduced $I_2$@SWNT sample.

The Auger peak at 510.0 eV is thus assigned to internally-loaded $I_2$, while those at 507.5 eV and 519.0 eV are attributed to externally-adsorbed $I_2$. The difference in the kinetic energies of these Auger emissions represents a definitive method of distinguishing between internal and external $I_2$. Auger parameters of 1138 eV are consistent with $I_2$, confirming once again that the external-adsorbed iodine is $I_2$, not a polyiodide or a C-I species. The shift observed in the Auger parameter, from 1138.5 eV to 1141 eV, for internal $I_2$, is likely due to the unique chemical environment experienced by $I_2$ confined within the interior of a SWNT.

Example 8

Inductively-coupled Plasma Analysis

The removal of iodine from the $I_2$-SWNTs during the Na0/THF reduction reaction was also confirmed by inductively-coupled plasma/atomic emission detector (ICP-AE) analysis of the THF/water filtrate. After the Na°/THF reaction was quenched with water, the reduced $I_2$@SWNTs were isolated by a glass frit filter. The THF/water filtrate was heated to remove the THF, and ICP-AE confirmed the presence of iodine (present as NaI) in the filtrate after the reduction reaction. A 20 mL sample contained 550 mg/L of I-, which corresponds to 10 mg of $I_2$ removed from the $I_2$-SWNT sample during the reduction reaction. This is consistent with the change observed in the atomic % of $I_2$ by XPS.

To confirm the stability of the internal $I_2$ with respect to chemical reduction, a second Na°/THF reaction was performed on the already reduced $I_2$-SWNTs (hereinafter $I_2$@SWNTs) under the same conditions. After a second Na°/THF reduction, 2.3 atomic % of iodine remained which is unchanged (within error) from the amount of $I_2$ present in the I2-SWNT sample after the first reduction. Additionally, the peak positions for iodine in the XPS and X-ray induced Auger emission spectra were unchanged from the peak positions after the first reduction (FIGS. 13 and 14) ICP-AE also confirmed that no iodine (as NaI) was present in the filtrate after the second reduction. These results establish that internal $I_2$ is truly sequestered within the interior of the nanotube ($I_2$@SWNTs) and is impervious to chemical reduction by Na°/THF.

Example 9

Variable-temperature XPS Studies

Variable-temperature XPS analysis was performed on an $I_2$-SWNT sample to assess the thermal stability of the internal $I_2$ vs. external $I_2$. A sample of the unreduced $I_2$-SWNTs was heated from room temperature to 800° C. under high vacuum. During this process, a mass spectrum analysis indicated $I_2^+$ (254 amu) and $I^+$ (127 amu) were the only positive ion species liberated from the $I_2$-SWNT sample in the temperature range of 200° C.-800° C. XPS spectra and X-ray induced Auger emission spectra were acquired every 100° C. As shown in FIG. 12a, a linear loss of iodine is observed by XPS from room temperature until 300° C. From 300° C. to 500° C., the iodine content remains constant, and above 500° C. linear loss of iodine is again observed. The atomic % of iodine remaining at 400° C. is ~2.0%, a value consistent with the amount of internally-loaded $I_2$ from the reduction experiments. As also shown in FIG. 12b, the X-ray induced Auger emission spectra of the $I_2$-SWNTs at room temperature (black), 100° C. (green), 200° C. (blue), 300° C. (red), and after the Na°/THF reduction reaction (yellow) confirm that the decrease in the atomic % of iodine observed by XPS is due to the removal of exterior-adsorbed $I_2$. The Auger peaks at 507.5 eV and 519.0 eV, assigned above to externally-adsorbed $I_2$, decrease in intensity from room temperature until their disappearance at ~300° C. This is illustrated by the shift from an unresolved doublet in the 505-510 eV region at room temperature (black trace in FIG. 9b, maxima at 507.5 eV and 510 eV) to a single peak at 300° C. (red trace in FIG. 12b, maximum at 510 eV). As discussed above, a shoulder is once again observed at ~517 eV after the external $I_2$ is removed from the SWNT sample (red trace in FIG. 12b). The Auger peak at 510.0 eV, assigned to internal $I_2$, is largely unchanged during the temperature study. The Auger emission spectrum of $I_2$-SWNTs at 300° C. (red trace in FIG. 12b) and the spectrum for reduced $I_2$@SWNTs (yellow trace in FIG. 12b) are identical with respect to the features at 507.5 and 519.0 eV. Heating to 300° C. thus provides an alternative method for removing externally-adsorbed $I_2$. It is possible to also remove the interior $I_2$ from the SWNT sample, but temperatures upwards of 800° C. are required.

Example 10

Raman Spectroscopy of Na°/THF Reduced $I_2$-SWNTs

Raman spectroscopy is used to characterize changes in the I-I stretching mode present in the $I_2$-SWNT sample as a result of the removal of external $I_2$, either by heating or Na°/THF reduction. As discussed above and shown in FIG. 15, there is an additional band at 159 cm$^{-1}$ in the Raman spectrum of $I_2$-SWNTs (FIG. 15b), which is not present in the raw SWNT spectrum (FIG. 15a). This band is therefore assigned to the v(I-I) stretching mode. Interestingly, this v(I-I) stretching mode decreases significantly when the $I_2$-SWNTs are reduced by the Na°/THF reduction reaction or heated to 400° C. (FIGS. 15c and 15d respectively). Upon heating to 1000° C., which removes all $I_2$, the 159 cm$^{-1}$ band completely disappears (FIG. 15e) and the Raman spectrum is once again identical to that for the raw SWNT sample (FIG. 15a). Thus, Raman spectroscopy can also be used to discriminate between internal and external $I_2$, by way of the relative intensities of the v(I-I) stretching mode, but only in conjunction with XPS spectral data.

Example 11

Micro Computed Tomography (MicroCT)

Finally, MicroCT experiments confirm that $I_2$@SWNTs are functional computed tomography contrast agents. Solid samples of raw SWNTs, $I_2$-SWNTs, and Na°/THF reduced $I_2$@SWNTs were placed in a cylindrical polyethylene holder and analyzed by a Skyscan 1172 microcomputed tomography scanner. The raw SWNTs, as expected, exhibit very little X-ray attenuation; qualitatively, raw SWNTs appear similar to the polyethylene holder. The attenuation for raw SWNTs, which contain no iodine, is most likely due to the presence of iron catalyst particles which also scatter X-rays, although not nearly as effectively as iodine (26 electrons for iron compared to 57 for iodine). The $I_2$-SWNTs, on the other hand, display extremely high attenuation. $I_2$@SWNTs, as expected, demonstrate much higher attenuation than the raw SWNTs, but not as high as the $I_2$-SWNTs. This is, of course, because $I_2$-SWNTs contain both internal and external $I_2$ (5.3 atomic %) whereas $I_2$@SWNTs contain only internal $I_2$ (2.8 atomic %). Comparative 2-D MicroCT images for raw SWNTs, $I_2$-SWNTs, and $I_2$@SWNTs are shown in FIGS. 16 and 32.

To quantify the performance of each sample, Hounsfield Units (HU) were calculated. The Hounsfield scale, established by Sir Godfrey Hounsfield, one of the developers of computed tomography, is a quantitative way of describing radiodensity. Specifically, distilled water is defined as 0 HU and air is defined as –1000 HU. Using these values, Hounsfield units of 14,927 HU, 46,438 HU, and 28,400 HU were calculated for raw SWNTs, $I_2$-SWNTs and $I_2$@SWNTs, respectively.

Example 12

Modified Approach Using Fluorination for Purification

US-tubes, with lengths ranging from 20-80 nm, were prepared via a modification of a known process. Currently, full-length SWNTs are cut into short pieces by a four-step process. First, residual iron catalyst particles are removed by oxidation via exposure to wet-air or $SF_6$ followed by a strong acid (HCl) treatment to extract the oxidized iron particles. The purified SWNTs are then fluorinated by a gaseous mixture of 1% $F_2$ in He at elevated temperatures for up to 2 hours and cut into short pieces by pyrolysis under argon at 900° C. The fluorination reaction produces F-SWNTs, with a stoichiometry of $CF_x$ (x<0.2), which consist of bands of fluorinated-SWNT separated by regions of pristine SWNT. Pyrolysis under Ar liberates volatile fluorocarbons, thereby cutting the SWNTs into pieces with lengths corresponding to the areas of pristine SWNT. While this method is effective at producing cut SWNTs, improvements can be made; specifically, the separate purification step is unnecessary and can be eliminated.

US-tubes were prepared via a three-step process. First, as produced HiPco SWNTs are fluorinated in a monel steel apparatus by a mixture of 1% $F_2$ in He at 100° C. for 2 hours. During this process, both the SWNTs and the iron catalyst particles become fluorinated. Subsequent exposure to concentrated HCl removes the fluorinated catalyst particles without affecting the F-SWNTs, which have a stoichiometry of ~$C_{10}F$ after the acid treatment. The, now-purified, F-SWNTs are cut into US-tubes by pyrolysis under Ar at 900° C. The resulting US-tubes have lengths ranging from 20-80 nm, with the majority being ~40 nm in length. Utilizing this method, the amount of iron catalyst is reduced from ~25 mass percent in raw SWNTs to ~1 mass percent for US-tubes. Therefore, this method is ideal for the purification of SWNTs, but only as a precursor to producing US-tubes. This is because the fluorine remaining, after the HCl acid treatment, is very hard to remove, making the F-SWNTs only viable for subsequent cutting.

Example 13

Atomic Force Microscopy of US-Tubes

Atomic force microscopy (AFM) analysis of the US-tubes illustrates the effectiveness of the cutting process. Shown in FIG. 17, all US-tubes are between 20 and 80 nm in length, with the majority being ~40 nm. No evidence of SWNTs longer than 100 nm can be found. Height measurements (FIG. 18) confirm that the US-tubes exist as small bundles, with heights between 3 and 7 nm.

Example 14

Raman Spectroscopy of US-tubes

Raman spectroscopy evaluates the structural changes to the SWNT resulting from the cutting procedure. The increase in the band at 1350 cm$^{-1}$, indicative of sp$^3$-hybridized carbon, confirms additional sidewall defects are created as a result of the cutting process. Comparative Raman spectra for SWNTs and US-tubes are shown in FIG. 19.

Atomic force microscopy also confirms that the Na°/THF reduction reaction debundles empty US-tubes into individuals. Shown in FIG. 20, height measurements substantiate individual US-tubes (diameters of ~1 nm). This is a significant result because it represents the first example of individual US-tubes in suspension. This is critical to the sidewall functionalization of US-tubes.

Example 15

Loading Procedures for US-tubes

The loading and characterization procedures of US-tubes are taken directly from the full-length SWNT model system. Loading of US-tubes is again accomplished via sublimation of I$_2$ in a closed glass vessel at 100° C. The mass gain observed for US-tubes is slightly higher than that observed for full-length SWNTs; typically a 50 mg sample of US-tubes increases 100-120% by mass during the loading process (final mass=100-110 mg) as opposed to the 80% mass increase observed for full-length SWNTs. This is likely due to the increased surface area of the US-tubes as compared to full-length SWNTs. XPS also confirms that I$_2$-US-tubes contain a greater amount of iodine than do I$_2$-SWNTs. Values of 8-9 atomic % iodine (~57% iodine by mass) are obtained for I$_2$-US-tubes in contrast to 5.3 atomic % for I$_2$-SWNTs (36% iodine by mass). This increase in atomic percent iodine is once again consistent with the mass increase observed during the I$_2$ sublimation process. The Raman spectrum for I$_2$-US-tubes, shown in FIG. 21, displays the peak, at 159 cm$^{-1}$, proven to be the v(I-I) stretching mode, once more confirming the presence of I$_2$.

Example 16

XPS of I$_2$-US-tubes

The I 3d$_{5/2}$ peak position, shown in FIG. 22, for I$_2$-US-tubes is 619.2±0.2 eV, consistent with both the I$_2$-SWNT data and accepted values for I$_2$ from the literature. The X-ray induced Auger emission spectrum for I$_2$-US-tubes, also shown in FIG. 22, again shows the same general features as I$_2$-SWNTs. Peaks are once again observed at 507.5 eV and 519 eV, with a shoulder at 510 eV. Thus, US-tubes and full-length SWNTs behave identically with respect to the loading process; however, the stability of the internal I$_2$ is dramatically reduced for I$_2$-US-tubes.

In the case of full-length SWNTs, the internal I$_2$ is remarkably stable with respect to either chemical reduction or elevated temperatures. In contrast, the internal I$_2$ in I$_2$-US-tubes is completely removed by either the Na°/THF reduction reaction or temperatures above 300° C. This is likely a consequence of the sidewall defects created during the cutting process, which allows Na°(Na°→Na$^+$+e$^-$) access to the US-tube interior and permits escape of internal I$_2$ from the US-tube at elevated temperatures.

Example 17

Raman Spectroscopy of Na°/THF Reduced I$_2$-US-tubes

I$_2$-US-tubes were reduced via the Na°/THF reaction using the same conditions described previously for I$_2$-SWNTs. The Raman spectrum of the Na°/THF reduced I$_2$-US-tubes, shown in FIG. 19, exhibits no peak in the vicinity of 159 cm$^{-1}$, indicating complete removal of I$_2$. XPS analysis confirms no iodine present in the Na°/THF reduced I$_2$-US-tubes. Therefore, the Na°/THF reduction of I$_2$-US-tubes to remove external I$_2$ is not a viable option, because the reduction also removes the internal I$_2$.

Comparing empty US-tubes (FIG. 16a) and empty SWNTs (FIG. 11a); it is apparent that empty SWNTs demonstrate higher X-ray attenuation. This is because iron catalyst particles, which scatter X-rays, are present in raw SWNTs but are removed during the preparation of US-tubes. Thus, US-tubes are very poor at attenuating X-rays and have a radiodensity of only 4366 HU. In stark contrast, I$_2$-US-tubes, which contain 57 mass % iodine by XPS, exhibit extraordinary X-ray attenuation. The radiodensity of I$_2$-US-tubes, again as a solid, is 43,716 HU. Even though this value is actually less than that of I$_2$-SWNTs (FIG. 11b, radiodensity=46,438 HU), I$_2$-US-tubes are likely superior X-ray attenuators due to their greater amount of iodine. In these experiments, the radiodensities of I$_2$-SWNTs and I$_2$-US-tubes are similar only because both attenuate the X-ray beam the maximum that can be measured.

I$_2$-US-tubes which have been reduced by the Na°/THF reaction are shown in FIG. 16c. As expected based on the previous XPS and Raman results, very little X-ray attenuation is demonstrated because all I$_2$ has been removed by the Na°/THF reduction reaction. The radiodensity of the Na°/THF reduced I$_2$-US-tubes is only 4395 HU as opposed to the 28,400 HU obtained for Na°/THF reduced I$_2$-SWNTs (FIG. 14c).

Example 18

Variable-Temperature XPS Study on I$_2$-US-tubes

An XPS temperature study demonstrates that elevated temperatures also result in the removal of internal I$_2$ from I$_2$-US-tubes. The atomic percent of iodine in I$_2$-US-tubes, as shown in FIG. 21, decreases much more rapidly with respect to temperature as compared to I$_2$-SWNTs. By 300° C., a temperature at which 2.8 atomic % of internal I$_2$ still remains in I$_2$-SWNTs, nearly all I$_2$ has been removed from I$_2$-US-tubes. The X-ray induced Auger emission temperature study, also shown in FIG. 18, does provide encouraging results. The same behavior exhibited by I$_2$-SWNTs, the disappearance of the X-ray induced Auger peaks at 507.5 and 519 eV as external I$_2$ is removed and the relative stability of the internal I$_2$ peak at 510 eV, is also demonstrated by I$_2$-US-tubes, albeit at lower temperatures. Thus, in spite of the sidewall defects present in US-tubes, the internal I$_2$ is more stable than external I$_2$, at least with respect to temperature.

While careful heating could provide a method of producing internally-loaded I$_2$@US-tubes, a chemical reduction method that does not remove internal I$_2$ would seem more advantageous, particularly with respect to functionalization of the I$_2$@US-tubes. US-tubes, even more so than full-length SWNTs, are very difficult to suspend in any solvent. Full-length SWNTs can be suspended, as individual tubes, in aqueous solvents via surfactant wrapping and, in both organic and aqueous solvents via Na°/THF reduction, thereby allowing functionalization reactions to take place on individual SWNTs as opposed to bundled SWNTs. US-tubes, in contrast, can not be suspended via surfactant wrapping and, as illustrated above, the Na°/THF reaction can not be used to suspend $I_2$-US-tubes. Therefore, it is imperative that an alternate chemical reduction method be found that does not remove the internal $I_2$ from $I_2$-US-tubes.

Example 19

NaH Reduction of $I_2$-US-tubes

Fortunately, experimentation with NaH, a reducing agent used as the first step in the Bingel cyclopropanation reaction, suggests that $I_2$ remains in the $I_2$-US-tubes after exposure to NaH for 1 hour. In a typical experiment, 10 mg $I_2$-US-tubes are added to a round bottom flask containing 20 mL toluene in a dry box. Then, 20 mg dimethylsulfoxide, DMSO, and 40 mg NaH are added to the flask and the reaction is allowed to proceed for one hour. After one hour, the reaction is quenched by the careful addition of ethanol. The reduced $I_2$@US-tubes are then isolated by filtration on a glass frit filter, washed with three 10 mL portions of EtOH and dried overnight at 40° C.

Example 20

Raman Spectroscopy of NaH Reduced $I_2$-US-tubes

Raman analysis reveals that $I_2$ remains after the NaH reduction. Shown in FIG. 23 are comparative Raman spectra for (a) Na°/THF reduced $I_2$-US-tubes, (b) NaH reduced $I_2$@US-tubes, and (c) Na°/THF reduced full-length $I_2$@SWNTs containing only internal $I_2$. The spectrum for the NaH reduced $I_2$@US-tubes exhibits a similar peak at 159 cm$^{-1}$ as the Na°/THF reduced $I_2$@SWNTs. The Na°/THF reduced $I_2$-US-tubes, in contrast, exhibit no such peak. Thus, Raman spectroscopy indicates that $I_2$, most likely internal $I_2$, survives a 1 hour NaH reduction reaction.

Example 21

Micro CT of Na°/THF Reduced $I_2$-US-tubes

Micro computed tomography (MicroCT) experiments illustrate the extremely high X-ray attenuation of $I_2$-US-tubes and the low X-ray attenuation of Na°/THF reduced $I_2$-US-tubes which, as a result of the Na°/THF reduction, no longer contain $I_2$. Shown in FIG. 24 are MicroCT images of a) empty US-tubes, b) $I_2$-US-tubes, and c) Na°/THF reduced $I_2$-US-tubes.

Comparing empty US-tubes (FIG. 24a) and empty SWNTs (FIG. 14a); it is apparent that empty SWNTs demonstrate higher X-ray attenuation. This is because iron catalyst particles, which scatter X-rays, are present in raw SWNTs but are removed during the preparation of US-tubes. Thus, US-tubes are very poor at attenuating X-rays and have a radiodensity of only 4366 HU. In stark contrast, $I_2$-US-tubes, which contain 57 mass % iodine by XPS, exhibit extraordinary X-ray attenuation. The radiodensity of $I_2$-US-tubes, again as a solid, is 43,716 HU. Even though this value is actually less than that of $I_2$-SWNTs (FIG. 14b, radiodensity=46,438 HU), $I_2$-US-tubes are likely superior X-ray attenuators due to their greater amount of iodine. In these experiments, the radiodensities of $I_2$-SWNTs and $I_2$-US-tubes are similar only because both attenuate the X-ray beam the maximum that can be measured.

$I_2$-US-tubes which have been reduced by the Na°/THF reaction are shown in FIG. 24c. As expected based on the previous XPS and Raman results, very little X-ray attenuation is demonstrated because all $I_2$ has been removed by the Na°/THF reduction reaction. The radiodensity of the Na°/THF reduced $I_2$-US-tubes is only 4395 HU as opposed to the 28,400 HU obtained for Na°/THF reduced $I_2$-SWNTs (FIG. 16c).

Example 22

Variable-Temperature XPS Study on $I_2$-US-tubes

An XPS temperature study demonstrates that elevated temperatures also result in the removal of internal $I_2$ from $I_2$-US-tubes. The atomic percent of iodine in $I_2$-US-tubes, as shown in FIG. 25I, decreases much more rapidly with respect to temperature as compared to $I_2$-SWNTs. By 300° C., a temperature at which 2.8 atomic % of internal $I_2$ still remains in $I_2$-SWNTs, nearly all $I_2$ has been removed from $I_2$-US-tubes. The X-ray induced Auger emission temperature study, also shown in FIG. 25, does provide encouraging results. The same behavior exhibited by $I_2$-SWNTs, the disappearance of the X-ray induced Auger peaks at 507.5 and 519 eV as external $I_2$ is removed and the relative stability of the internal $I_2$ peak at 510 eV, is also demonstrated by $I_2$-US-tubes, albeit at lower temperatures. Thus, in spite of the sidewall defects present in US-tubes, the internal $I_2$ is more stable than external $I_2$, at least with respect to temperature.

Example 23

NaH Reduction of $I_2$-US-tubes

Fortunately, experimentation with NaH, a reducing agent used as the first step in the Bingel cyclopropanation reaction, suggests that $I_2$ remains in the $I_2$-US-tubes after exposure to NaH for 1 hour. In a typical experiment, 10 mg $I_2$-US-tubes are added to a round bottom flask containing 20 mL toluene in a dry box. Then, 20 mg dimethylsulfoxide, DMSO, and 40 mg NaH are added to the flask and the reaction is allowed to proceed for one hour. After one hour, the reaction is quenched by the careful addition of ethanol. The reduced $I_2$@US-tubes are then isolated by filtration on a glass frit filter, washed with three 10 mL portions of EtOH and dried overnight at 40° C.

Example 24

Raman Spectroscopy of NaH Reduced $I_2$-US-tubes

Raman analysis reveals that $I_2$ remains after the NaH reduction. Shown in FIG. 26 are comparative Raman spectra for (a) Na°/THF reduced $I_2$-US-tubes, (b) NaH reduced b@US-tubes, and (c) Na°/THF reduced full-length $I_2$@SWNTs containing only internal $I_2$. The spectrum for the NaH reduced $I_2$@US-tubes exhibits a similar peak at 159 cm$^{-1}$ as the Na°/THF reduced b@SWNTs. The Na°/THF reduced $I_2$-US-tubes, in contrast, exhibit no such peak. Thus, Raman spectroscopy indicates that $I_2$, most likely internal $I_2$, survives a 1 hour NaH reduction reaction.

Example 25

XPS of NaH Reduced $I_2$-US-tubes

This indication is confirmed by XPS and X-ray induced Auger spectral analysis. XPS analysis verifies that 1.3 atomic % iodine remains in the NaH reduced $I_2$@US-tubes. The position of the I $3d_{5/2}$ peak in the XPS spectrum of NaH reduced $I_2$@US-tubes is 619.2±0.2 eV, consistent with all previous measurements (FIG. 27). The X-ray induced Auger emission spectrum of NaH reduced $I_2$@US-tubes contains one peak, at 510 eV, with a visible shoulder at ~515 eV as shown in FIG. 27. This is consistent with the X-ray induced Auger emission spectrum, shown in FIG. 11, of Na°/THF reduced $I_2$@SWNTs which contain only internal $I_2$; thus, the NaH reduced $I_2$@US-tubes also contain only internal $I_2$. The $13d_{5/2}$ XPS spectrum and X-ray induced Auger emission spectrum of NaH reduced $I_2$@US-tubes are shown in FIG. 23. Unfortunately, unlike $I_2$@SWNTs, which do not lose additional $I_2$ with repeated reduction treatments or extended exposure to the reduction reagent, the internal $I_2$ stability of $I_2$@US-tubes is short-lived. As described above, the NaH reduction reaction is quenched after one hour and, under these conditions, $I_2$ remains. However, if the reaction is allowed to proceed for 24 hours, all $I_2$ is removed. Therefore, given enough time, the internal $I_2$ in $I_2$@US-tubes is accessible to the NaH reduction. This result has important consequences for $I_2$@US-tube sidewall functionalization reactions.

Example 26

$I_2$ Loading Before PEG Functionalization

The first attempt at synthesizing PEG-$I_2$@SWNTs involves first loading US-tubes with $I_2$ followed by sidewall functionalization of the $I_2$-US-tubes with PEG using the reaction scheme shown in FIG. 28. This would be the ideal method of producing PEG-$I_2$@US-tubes because it would unequivocally ensure that any $I_2$ present in the final product is contained within the interior of the US-tube. The first step of this method, the attachment of diethyl malonate, requires the presence of NaH which also removes all external $I_2$. Thus, there would be no risk of $I_2$ interfering with subsequent reactions or reacting with PEG itself. Unfortunately, the attachment of the diethyl malonate requires overnight exposure to NaH and, this results in the complete removal of all $I_2$. A one hour reaction, which does leave some internal $I_2$, is insufficient and does not result derivatization with diethyl malonate groups. XPS measurements confirm that no iodine is seen in the final product using this method. To counteract the removal of all $I_2$ by NaH, an alternate method of diethyl malonate attachment can be used, as shown in FIG. 29.

Example 27

$I_2$ Loading Before Alternate PEG Functionalization

This method circumvents the problem of 24 hour exposure of $I_2$@US-tubes to NaH by utilizing an alternate functionalization method. In this method, initial attachment of the diethyl malonate groups is achieved by a reaction with carbon tetrabromide ($CBr_4$) and 1,8-Diazabicyclo[5.4.0]undec-7-ene (DBU), a strong organic base, in THF. For this method, US-tubes are again loaded with $I_2$ prior to any functionalization reactions. Unfortunately, as mentioned previously, US-tubes are extremely difficult to suspend in any solvent. In fact, the only known method of suspending US-tubes in THF, or any organic solvent for that matter, is, of course, chemical reduction, which cannot be performed on $I_2$-US-tubes without removal of all $I_2$. Sonication of the $I_2$-US-tubes for 1 hour in several organic solvents, without the presence of a reducing agent, did not result in suspension of the $I_2$-US-tubes, therefore the diethyl malonate reaction could not occur.

This method was also attempted with US-tubes which were first reduced by the Na°/THF reaction prior to $I_2$ loading, but this was also unsuccessful. While empty US-tubes are usually able to be resuspended after the Na°/THF reduction and subsequent drying, US-tubes which were Na°/THF reduced, then loaded with $I_2$ did not resuspended in organic solvents with sonication. It is unclear, but likely, that the $I_2$ loading process resulted in the inability to resuspended the reduced $I_2$-US-tubes. Regardless, these attempts illustrate that $I_2$ is not stable enough within the interior of a US-tube to survive Bingel reaction conditions. Therefore, even though $I_2$ loading after the PEGylation of the US-tubes is not the ideal scenario, the instability of the internal $I_2$ necessitates this approach.

Example 28

$I_2$ Loading after Complete PEG Functionalization

The $I_2$ loading of PEG-US-tubes is not an ideal method for three reasons. First, the PEG groups are bulky and may prevent $I_2$ from entering the SWNT. Second, since $I_2$ loading is the last step in this process, additional washing steps and characterization must be performed to ensure that any $I_2$ present is contained within the SWNT and not adsorbed to the exterior. Finally, experiments must be developed to make certain that $I_2$ does not react with the PEG itself. Nevertheless, US-tubes were first functionalized with PEG via the Bingel reactions (FIG. 28). The PEG-US-tubes were then isolated using a glass frit filter and dried overnight. Solid PEG-US-tubes were then subjected to $I_2$ loading conditions as described previously and washed with three 20 mL portions of ethanol to remove excess $I_2$. The first two ethanol washings produced a dark orange and pale yellow color, respectively, indicative of $I_2$. The third ethanol washing did not produce any color, indicating excess $I_2$ removal was complete. However, XPS of the PEG-$I_2$-US-tubes indicated no iodine present. Therefore, it can be concluded that the PEG groups prevent $I_2$ access to the US-tube interior. It can also be deduced that $I_2$ does not react with the hydroxyl groups in PEG, which is important for future experiments involving serinol amide-$I_2$@US-tubes. These three methods demonstrate that $I_2$ loading cannot be either the first or last step in the PEG functionalization process. Therefore, the only logical choice remaining is $I_2$ loading between steps of the Bingel reactions.

Example 29

$I_2$ Loading after Diethyl Malonate Reaction

Since this reaction scheme (FIG. 28) is a three step process and previous attempts have illustrated that $I_2$ loading cannot occur either before the first step or after the last step, only two choices remain; $I_2$ loading after the attachment of diethyl malonate or after conversion of the diethyl malonate to acid chloride. Because taking an acid chloride to dryness is generally a bad idea, only one logical choice remains. Thus the fourth and final attempt to synthesize PEG-$I_2$@US-tubes involves performing the diethyl malonate functionalization on empty US-tubes, followed by $I_2$ loading. After $I_2$ loading, excess $I_2$ is removed by washing with ethanol then the acid chloride and PEGylation reactions are performed.

First, US-tubes are functionalized with diethyl malonate via Reaction 1 in FIG. 28. The resulting product is again isolated using a glass frit filter, dried overnight, then loaded with $I_2$ via sublimation. XPS confirms that these diethyl malonate-US-tubes load with $I_2$, unlike PEG-US-tubes; 5.6 atomic % iodine is present after the loading process. However, after three washings with 20 mL portions of ethanol, 0 atomic % iodine is measured by XPS. It is unclear whether the iodine present after the loading of diethyl malonate-US-tubes is all externally-adsorbed, which would explain its easy removal, or if $I_2$ is contained within the diethyl malonate-US-tubes, but removed by ethanol washing. Regardless, the $I_2$ does not survive the remaining reactions and XPS confirms no iodine remaining in the PEG-US-tubes utilizing this method.

Example 30

$I_2$ Loaded US Tubes Substituted with Serinol Groups $I_2$ loaded US-tubes substituted with serinol groups have been made by performing the serinol functionalization on empty US-tubes as shown by the reaction scheme in FIG. 30. Then the functionalized US-tubes are filled with $I_2$ via sublimation as described above. External $I_2$ is removed by a very short (10 minute) exposure to NaH. XPS and XAES analyses confirm that iodine remains after the reduction, that it is only internal $I_2$, and that the serinol moieties are not affected. The final product contains 1.2 atomic % iodine, or about 10% by weight.

The XPS and XAES spectra (FIGS. 33 and 34) which give the atomic % iodine and prove that it is only internally-loaded $I_2$ due to the disappearance of the XAES peaks at 507.5 eV and 519 eV, which illustrates the removal of external $I_2$. The peak at 510 eV is due to internal $I_2$. The nitrogen % in the XPS data is due to the serinol amide moiety.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method for preparing an imaging agent comprising:
   providing a carbon nanotube, wherein the carbon nanotube is selected from the group consisting of a single walled carbon nanotube and an ultra short carbon nanotube;
   loading the carbon nanotube with $I_2$, wherein the loading is performed in a manner sufficient to sequester the $I_2$ within the carbon nanotube; and
   removing the $I_2$ from the exterior of the carbon nanotube thereby yielding the imaging agent.

2. The method of claim 1 wherein the carbon nanotube is substituted.

3. A method for preparing an imaging agent comprising:
   providing a carbon nanotube, wherein the carbon nanotube is selected from the group consisting of a single walled carbon nanotube and an ultra short carbon nanotube;
   loading the carbon nanotube with a contrast agent, wherein the loading is performed by sublimation to sequester the contrast agent within the carbon nanotube; and
   removing the contrast agent from the exterior of the carbon nanotube thereby yielding the imaging agent.

4. The method of claim 3 wherein the carbon nanotube is substituted.

5. The method of claim 3 wherein the contrast agent is $I_2$.

* * * * *